(12) United States Patent
Goodis

(10) Patent No.: US 10,052,173 B2
(45) Date of Patent: Aug. 21, 2018

(54) ENDODONTIC FILES AND OBTURATOR DEVICES AND METHODS OF MANUFACTURING SAME

(75) Inventor: Charles J. Goodis, Albuquerque, NM (US)

(73) Assignee: GUIDANCE ENDODONTICS, LLC, Albuquerque, NM (US)

( * ) Notice: Subject to any disclaimer, the term of this patent is extended or adjusted under 35 U.S.C. 154(b) by 0 days.

(21) Appl. No.: 13/016,050

(22) Filed: Jan. 28, 2011

(65) Prior Publication Data

US 2011/0129793 A1 Jun. 2, 2011

Related U.S. Application Data

(62) Division of application No. 11/081,974, filed on Mar. 16, 2005, now Pat. No. 7,967,605.
(Continued)

(51) Int. Cl.
*A61C 5/08* (2006.01)
*A61C 5/50* (2017.01)
(Continued)

(52) U.S. Cl.
CPC .......... *A61C 5/50* (2017.02); *A61C 5/42* (2017.02); *A61C 5/44* (2017.02)

(58) Field of Classification Search
CPC .......... A61C 5/023; A61C 5/04; A61C 5/025
(Continued)

(56) References Cited

U.S. PATENT DOCUMENTS 503,744 A 8/1893 How
626,359 A 6/1899 Atlee
(Continued)

FOREIGN PATENT DOCUMENTS

CA 1275836 11/1990
CA 2 199 685 9/1997
(Continued)

OTHER PUBLICATIONS

"A short history of the dental drill," Journal of the American Dental Association 108(4): 572-573 (Apr. 1984).
Altuna, G. et al., "A statistical assessment of orthodontic practices, product usage, and the development of skin lesions," American Journal of Orthodontics and Dentofacial Orthopedics 100(3): 242-250 (Sep. 1991).
Angolkar, P.V. et al., "Evaluation of friction between ceramic brackets and orthodontic wires of four alloys," American Journal of Orthodontics and Dentofacial Orthopedics 98(6): 499-506 (Dec. 1990).
Breyer, R.H. et al., "Myocardial biopsy drill: construction details and techniques," Journal of Surgical Research 38(3): 134-137 (Feb. 1985).
(Continued)

*Primary Examiner* — Ralph Lewis
(74) *Attorney, Agent, or Firm* — Hunton Andrews Kurth LLP

(57) ABSTRACT

An endodontic file, or a series of endodontic files, and an endodontic obturator or series of obturators, and methods of manufacturing same. Regarding the endodontic files, they may include a file body extending from a tip region to a shank region, at least one helical flute extending from the tip region towards the shank region. Each helical flute may have an up-sharp cutting edge without a land. For one such set of endodontic files, there is included at least a first and a second file, each one of the files having a tip and a shank, the first file having a tip size that is substantially the same as a tip size of the second file, wherein the first file has a different taper configuration relative to the taper configuration of the second file. The taper configurations of each one of the first and second files include at least two different rates of taper, the taper configurations of each one of the first and second files arranged such that at least one rate of taper closer to the shank of the file is smaller than at least one rate of taper closer to a tip of the file.

9 Claims, 10 Drawing Sheets

Related U.S. Application Data

(60) Provisional application No. 60/553,792, filed on Mar. 16, 2004, provisional application No. 60/648,099, filed on Jan. 28, 2005, provisional application No. 60/648,167, filed on Jan. 28, 2005.

(51) Int. Cl.
  *A61C 5/42* (2017.01)
  *A61C 5/44* (2017.01)

(58) Field of Classification Search
  USPC .......................................... 433/81, 102, 224
  See application file for complete search history.

(56) References Cited

U.S. PATENT DOCUMENTS

| | | |
|---|---|---|
| 636,359 A | 11/1899 | Schultz |
| 716,441 A | 12/1902 | Latham |
| 749,624 A | 1/1904 | McCullough |
| 1,067,015 A | 7/1913 | Fowler |
| 1,307,446 A | 6/1919 | Kerr |
| 2,715,772 A | 8/1955 | Fritz |
| 2,797,996 A | 7/1957 | Jaffe et al. |
| 2,885,838 A | 5/1959 | White et al. |
| 2,897,696 A | 8/1959 | Tisserant |
| 2,902,763 A | 9/1959 | Hoppe et al. |
| 2,990,369 A | 6/1961 | Shapiro et al. |
| 3,067,356 A | 12/1962 | Ray |
| 3,317,463 A | 5/1967 | Schonfeld et al. |
| 3,351,463 A | 11/1967 | Rozner et al. |
| 3,564,915 A | 2/1971 | Tomota et al. |
| 3,577,635 A | 5/1971 | Bergman et al. |
| 3,615,301 A | 10/1971 | Pike et al. |
| 3,636,947 A | 1/1972 | Balamuth |
| 3,645,642 A | 2/1972 | Koslow |
| 3,722,146 A | 3/1973 | Rodriguez et al. |
| 3,726,014 A | 4/1973 | Weissman |
| 3,758,222 A | 9/1973 | Oakes |
| 3,800,633 A | 4/1974 | Funakubo |
| 3,834,013 A | 9/1974 | Gerstle |
| 3,835,734 A | 9/1974 | Arthur et al. |
| 3,836,278 A | 9/1974 | McInnes |
| 3,837,848 A | 9/1974 | Wessel |
| 3,844,039 A | 10/1974 | Fleer et al. |
| 3,850,054 A | 11/1974 | Weissman |
| 3,857,181 A | 12/1974 | Rappaport |
| 3,863,345 A * | 2/1975 | Malmin ........................ 433/224 |
| 3,892,117 A | 7/1975 | Nelson |
| 3,892,232 A | 7/1975 | Neufeld |
| 3,921,298 A | 11/1975 | Fattaleh |
| 3,924,333 A | 12/1975 | Erickson |
| 3,932,055 A | 1/1976 | Flatland |
| 3,934,349 A | 1/1976 | Eibofner |
| 3,935,640 A | 2/1976 | Cohan |
| 3,944,782 A | 3/1976 | Metcalfe et al. |
| 3,955,283 A | 5/1976 | Mehallick |
| 3,955,284 A | 5/1976 | Balson |
| 3,969,823 A | 7/1976 | Nakanishi |
| 3,971,135 A | 7/1976 | Leu |
| 3,979,829 A | 9/1976 | Lemos |
| 3,980,849 A | 9/1976 | Straihammer |
| 3,983,344 A | 9/1976 | Straihammer |
| 3,984,213 A | 10/1976 | Kelso |
| 3,988,913 A | 11/1976 | Metcalfe et al. |
| 3,988,914 A | 11/1976 | Metcalfe et al. |
| 3,988,955 A | 11/1976 | Engel et al. |
| 3,990,332 A | 11/1976 | Flom et al. |
| 4,012,841 A | 3/1977 | Mosimann |
| 4,024,369 A | 5/1977 | Thompson et al. |
| 4,024,638 A | 5/1977 | Linkow et al. |
| 4,034,653 A | 7/1977 | Anderson |
| 4,037,324 A | 7/1977 | Andreasen |
| 4,040,129 A | 8/1977 | Steinemann et al. |
| 4,060,120 A | 11/1977 | Takahashi et al. |
| 4,069,587 A | 1/1978 | Peralta |
| 4,094,708 A | 6/1978 | Hubbard et al. |
| 4,114,275 A | 9/1978 | Jones et al. |
| 4,117,597 A | 10/1978 | Trist et al. |
| 4,117,791 A | 10/1978 | Current et al. |
| 4,123,845 A | 11/1978 | Fattaleh |
| 4,127,355 A | 11/1978 | Oakes |
| 4,158,746 A | 6/1979 | Taylor et al. |
| 4,169,173 A | 9/1979 | Bergholm et al. |
| 4,176,453 A | 12/1979 | Abbott |
| 4,185,385 A | 1/1980 | Simor |
| 4,185,386 A | 1/1980 | Nordin et al. |
| 4,189,266 A | 2/1980 | Koslow |
| 4,189,834 A | 2/1980 | Smith |
| 4,190,958 A | 3/1980 | Martin et al. |
| 4,193,196 A | 3/1980 | Kuris et al. |
| 4,194,860 A | 3/1980 | Hopkins |
| 4,197,643 A | 4/1980 | Burstone et al. |
| 4,199,160 A | 4/1980 | Bent |
| 4,205,444 A | 6/1980 | Weissman |
| 4,209,908 A | 7/1980 | Fleer |
| 4,219,620 A | 8/1980 | Carse |
| 4,221,152 A | 9/1980 | Jason |
| 4,231,737 A | 11/1980 | Groen |
| 4,231,738 A | 11/1980 | Riitano et al. |
| 4,240,789 A | 12/1980 | Rosenthaler |
| 4,243,388 A | 1/1981 | Arai |
| 4,253,830 A | 3/1981 | Kazen et al. |
| 4,260,379 A | 4/1981 | Groves et al. |
| 4,262,369 A | 4/1981 | Roux |
| 4,268,252 A | 5/1981 | Lustig |
| 4,274,070 A | 6/1981 | Thiene |
| 4,286,949 A | 9/1981 | Holt, Jr. |
| 4,286,950 A | 9/1981 | Hawk |
| 4,289,849 A | 9/1981 | Lustig et al. |
| 4,295,827 A | 10/1981 | Martin et al. |
| 4,299,571 A | 11/1981 | McSpadden |
| 4,306,866 A | 12/1981 | Weissman |
| 4,320,927 A | 3/1982 | Sertich |
| 4,327,156 A | 4/1982 | Dillon et al. |
| 4,330,278 A | 5/1982 | Martin |
| 4,332,561 A | 6/1982 | McSpadden |
| 4,340,364 A | 7/1982 | Deemer |
| 4,353,698 A | 10/1982 | McSpadden |
| 4,355,979 A | 10/1982 | Weissman |
| 4,359,318 A | 11/1982 | Gittleman |
| 4,365,958 A | 12/1982 | Vlock |
| 4,385,281 A | 5/1983 | McAlear et al. |
| 4,411,763 A | 10/1983 | Itaba et al. |
| 4,436,512 A | 3/1984 | Garcia |
| 4,443,193 A | 4/1984 | Roane |
| 4,445,611 A | 5/1984 | Shofu |
| 4,445,860 A | 5/1984 | Oehler |
| 4,450,834 A | 5/1984 | Fischer |
| 4,454,258 A | 6/1984 | Kawahara et al. |
| 4,457,710 A | 7/1984 | McSpadden |
| 4,464,113 A | 8/1984 | Parmley |
| 4,478,578 A | 10/1984 | Leonard |
| 4,502,150 A | 2/1985 | Katz et al. |
| 4,502,475 A | 3/1985 | Weigle et al. |
| 4,517,977 A | 5/1985 | Frost |
| 4,519,125 A | 5/1985 | Colonius et al. |
| 4,523,364 A | 6/1985 | Laws et al. |
| 4,534,734 A | 8/1985 | Lares |
| 4,538,989 A | 9/1985 | Apairo, Jr. et al. |
| 4,561,845 A | 12/1985 | Meller |
| 4,564,354 A | 1/1986 | Rosenstatter |
| 4,568,285 A | 2/1986 | Chiaramonte et al. |
| 4,568,398 A | 2/1986 | Wood et al. |
| 4,568,642 A | 2/1986 | DeForrest et al. |
| 4,571,180 A | 2/1986 | Kulick |
| 4,599,936 A | 7/1986 | Bedwell et al. |
| 4,600,392 A | 7/1986 | Weissman |
| 4,604,346 A | 8/1986 | Bell et al. |
| 4,604,884 A | 8/1986 | Matsutani |
| 4,608,972 A | 9/1986 | Small |
| 4,611,500 A | 9/1986 | Nagano |
| 4,611,509 A | 9/1986 | Matsutani |
| 4,619,696 A | 10/1986 | Gorgerino |
| 4,629,377 A | 12/1986 | Tlaker et al. |

(56) References Cited

U.S. PATENT DOCUMENTS

| | | |
|---|---|---|
| 4,632,093 A | 12/1986 | Giorni |
| 4,634,378 A | 1/1987 | Leonard |
| 4,642,051 A | 2/1987 | Lohn |
| 4,642,738 A | 2/1987 | Meller |
| 4,649,678 A | 3/1987 | Lamson |
| 4,655,710 A | 4/1987 | Andersson et al. |
| 4,661,061 A | 4/1987 | Martin |
| 4,661,067 A | 4/1987 | Harvey, Sr. et al. |
| 4,662,891 A | 5/1987 | Noiles |
| 4,673,317 A | 6/1987 | Haug |
| 4,673,550 A | 6/1987 | Dallaire et al. |
| 4,674,979 A | 6/1987 | Jacklich |
| 4,676,750 A | 6/1987 | Mason |
| 4,692,978 A | 9/1987 | Cunningham et al. |
| 4,706,659 A | 11/1987 | Matthews et al. |
| 4,708,655 A | 11/1987 | Weissman |
| 4,713,077 A | 12/1987 | Small |
| 4,718,051 A | 1/1988 | Ohshima et al. |
| 4,722,687 A | 2/1988 | Scortecci |
| 4,723,911 A | 2/1988 | Kurtz |
| 4,728,876 A | 3/1988 | Mongeon et al. |
| 4,730,880 A | 3/1988 | Schmidt et al. |
| 4,732,563 A | 3/1988 | Goof |
| 4,738,616 A | 4/1988 | Reynaud |
| 4,752,159 A | 6/1988 | Howlett |
| 4,768,757 A | 9/1988 | Nakamura et al. |
| 4,772,204 A | 9/1988 | Soderberg |
| 4,773,855 A | 9/1988 | Levy |
| 4,784,538 A | 11/1988 | Tlaker et al. |
| 4,784,907 A | 11/1988 | Matsufuji et al. |
| 4,786,251 A | 11/1988 | Ruegsegger |
| 4,787,907 A | 11/1988 | Carignan |
| 4,797,101 A | 1/1989 | Morris |
| 4,799,973 A | 1/1989 | Mahulikar et al. |
| 4,820,156 A | 4/1989 | Ross |
| 4,822,362 A | 4/1989 | Walker et al. |
| 4,824,370 A | 4/1989 | Laurichesse et al. |
| 4,830,823 A | 5/1989 | Nakamura |
| 4,836,780 A | 6/1989 | Buchanan |
| 4,838,786 A | 6/1989 | Reher et al. |
| 4,841,653 A | 6/1989 | Negley |
| RE32,972 E | 7/1989 | Harvey, Sr. et al. |
| 4,850,874 A | 7/1989 | Weissman |
| 4,856,867 A | 8/1989 | Gaylin |
| 4,857,269 A | 8/1989 | Wang et al. |
| 4,863,091 A | 9/1989 | Dubois |
| 4,867,305 A | 9/1989 | Schneider |
| 4,871,312 A | 10/1989 | Heath |
| 4,872,840 A | 10/1989 | Bori |
| 4,876,870 A | 10/1989 | Rantanen |
| 4,877,399 A | 10/1989 | Frank et al. |
| 4,878,842 A | 11/1989 | Malcmacher et al. |
| 4,889,487 A | 12/1989 | Lovaas |
| 4,894,011 A * | 1/1990 | Johnson .................. 433/81 |
| 4,894,100 A | 1/1990 | Yamauchi et al. |
| 4,895,515 A | 1/1990 | Axelsson |
| 4,897,037 A | 1/1990 | Appleby |
| 4,904,105 A | 2/1990 | Myers |
| 4,915,166 A | 4/1990 | Cunningham et al. |
| 4,927,421 A | 5/1990 | Goble et al. |
| 4,934,934 A | 6/1990 | Arpaio, Jr. et al. |
| 4,936,170 A | 6/1990 | Zumeta |
| 4,945,904 A | 8/1990 | Bolton et al. |
| 4,952,236 A | 8/1990 | Wang et al. |
| 4,957,550 A | 9/1990 | Reher et al. |
| 4,961,782 A | 10/1990 | Reher et al. |
| 4,973,247 A | 11/1990 | Varves et al. |
| 4,973,357 A | 11/1990 | Reher et al. |
| 4,976,625 A | 12/1990 | Weissman |
| 4,982,627 A | 1/1991 | Johnson |
| 4,983,121 A | 1/1991 | Straihammer et al. |
| 4,990,087 A | 2/1991 | De Rocchis et al. |
| 4,990,088 A | 2/1991 | Weissman |
| 4,992,049 A | 2/1991 | Weissman |
| 4,998,923 A | 3/1991 | Samson et al. |
| 4,999,952 A | 3/1991 | Speiser et al. |
| 5,009,596 A | 4/1991 | Soderberg |
| 5,011,511 A | 4/1991 | Beck |
| 5,017,138 A | 5/1991 | Schilder |
| 5,024,026 A | 6/1991 | Korb |
| 5,030,222 A | 7/1991 | Calandruccio et al. |
| 5,031,488 A | 7/1991 | Zumeta |
| 5,035,617 A | 7/1991 | McSpadden |
| 5,037,423 A | 8/1991 | Kenna |
| 5,037,426 A | 8/1991 | Goble et al. |
| 5,038,014 A | 8/1991 | Pratt et al. |
| 5,042,281 A | 8/1991 | Metcalfe |
| 5,046,948 A | 9/1991 | Miura |
| 5,047,034 A | 9/1991 | Sohngen |
| 5,048,235 A | 9/1991 | Smith |
| 5,049,716 A | 9/1991 | Dunmire et al. |
| 5,051,092 A | 9/1991 | Miller |
| 5,055,042 A | 10/1991 | Jansen |
| 5,061,181 A | 10/1991 | Niznick |
| 5,061,352 A | 10/1991 | Kelly et al. |
| 5,062,742 A | 11/1991 | Haug |
| 5,062,798 A | 11/1991 | Tsuge et al. |
| 5,065,549 A | 11/1991 | Speiser et al. |
| 5,066,230 A | 11/1991 | Weissman |
| 5,080,588 A | 1/1992 | O'Brien |
| 5,083,921 A | 1/1992 | Dragan |
| 5,085,586 A | 2/1992 | Johnson |
| 5,090,905 A | 2/1992 | Malata, Jr. |
| 5,104,316 A | 4/1992 | McSpadden |
| 5,106,298 A | 4/1992 | Heath et al. |
| 5,108,287 A | 4/1992 | Yee et al. |
| 5,110,297 A | 5/1992 | Teague |
| 5,112,336 A | 5/1992 | Krevolin et al. |
| 5,118,297 A | 6/1992 | Johnson |
| 5,125,838 A | 6/1992 | Seigneurin |
| 5,145,369 A | 9/1992 | Lustig et al. |
| 5,145,373 A | 9/1992 | Roane |
| 5,150,788 A | 9/1992 | Weissman |
| 5,153,006 A | 10/1992 | Hodosh |
| 5,154,611 A | 10/1992 | Calvin |
| 5,158,453 A | 10/1992 | Brockway |
| 5,182,895 A | 2/1993 | Lugo |
| 5,197,880 A | 3/1993 | Lovaas |
| 5,201,656 A | 4/1993 | Sicurelli, Jr. |
| 5,205,682 A | 4/1993 | Jinkins |
| 5,213,499 A | 5/1993 | Levy |
| 5,215,461 A | 6/1993 | Riazi |
| 5,216,845 A | 6/1993 | Buljan et al. |
| 5,217,372 A | 6/1993 | Truocchio |
| 5,219,284 A | 6/1993 | Velvart et al. |
| 5,219,285 A | 6/1993 | Meller et al. |
| 5,236,196 A | 8/1993 | Blankenburg et al. |
| 5,246,370 A | 9/1993 | Coatoam |
| 5,251,751 A | 10/1993 | Prussen |
| 5,261,818 A | 11/1993 | Shaw |
| 5,273,559 A | 12/1993 | Hammar et al. |
| 5,277,583 A | 1/1994 | Chalifoux |
| 5,295,830 A | 3/1994 | Shen et al. |
| 5,299,937 A | 4/1994 | Gow |
| 5,302,123 A | 4/1994 | Bechard |
| 5,308,242 A | 5/1994 | McLaughlin et al. |
| 5,312,253 A | 5/1994 | Chalifoux |
| 5,330,355 A | 7/1994 | Lietaer |
| 5,330,468 A | 7/1994 | Burkhart |
| 5,331,774 A | 7/1994 | Domenella |
| 5,334,013 A | 8/1994 | Meller |
| 5,338,195 A | 8/1994 | Flannagan |
| 5,376,444 A | 12/1994 | Grotepass et al. |
| 5,380,200 A | 1/1995 | Heath et al. |
| 5,387,059 A | 2/1995 | Borzemsky |
| 5,407,351 A | 4/1995 | Brockway |
| 5,415,546 A | 5/1995 | Cox, Sr. |
| 5,421,727 A | 6/1995 | Stevens et al. |
| 5,429,504 A | 7/1995 | Peltier et al. |
| 5,464,362 A | 11/1995 | Heath et al. |
| 5,498,158 A | 3/1996 | Wong |
| 5,503,554 A | 4/1996 | Schoeffel |
| 5,511,977 A | 4/1996 | Futch, Jr. |
| 5,514,144 A | 5/1996 | Bolton |

(56) References Cited

U.S. PATENT DOCUMENTS

| | | |
|---|---|---|
| 5,514,145 A | 5/1996 | Durham et al. |
| 5,518,399 A | 5/1996 | Sicurelli, Jr. et al. |
| 5,527,205 A | 6/1996 | Heath et al. |
| 5,531,596 A | 7/1996 | Melde |
| 5,533,097 A | 7/1996 | Crane et al. |
| 5,538,423 A | 7/1996 | Coss et al. |
| 5,538,425 A | 7/1996 | Reeves et al. |
| 5,553,675 A | 9/1996 | Pitzen et al. |
| 5,569,035 A | 10/1996 | Balfour et al. |
| 5,575,646 A | 11/1996 | Giannella |
| 5,575,650 A | 11/1996 | Niznick et al. |
| 5,575,657 A * | 11/1996 | Welch ............ 433/224 |
| 5,586,885 A | 12/1996 | Kert |
| 5,599,184 A | 2/1997 | Field |
| 5,605,460 A | 2/1997 | Heath et al. |
| 5,613,852 A | 3/1997 | Bavitz |
| 5,624,259 A | 4/1997 | Heath et al. |
| 5,628,674 A | 5/1997 | Heath et al. |
| 5,632,620 A | 5/1997 | Musikant et al. |
| 5,642,998 A | 7/1997 | Riitano |
| 5,653,590 A | 8/1997 | Heath et al. |
| 5,658,145 A | 8/1997 | Maillefer et al. |
| 5,658,149 A | 8/1997 | Munce |
| 5,669,772 A | 9/1997 | Musikant et al. |
| 5,676,542 A | 10/1997 | Lingenhole et al. |
| 5,676,593 A | 10/1997 | Stevens |
| 5,689,159 A | 11/1997 | Culp et al. |
| 5,695,513 A | 12/1997 | Johnson et al. |
| 5,700,184 A | 12/1997 | Domenella |
| 5,707,375 A | 1/1998 | Durham et al. |
| 5,713,736 A | 2/1998 | Heath et al. |
| 5,716,210 A | 2/1998 | Novak |
| 5,735,689 A | 4/1998 | McSpadden |
| 5,735,690 A | 4/1998 | Malentacca |
| 5,741,139 A | 4/1998 | Sicurelli, Jr. et al. |
| 5,746,597 A | 5/1998 | Maillefer et al. |
| 5,752,825 A | 5/1998 | Buchanan |
| 5,762,497 A | 6/1998 | Heath |
| 5,762,498 A | 6/1998 | Gonzalez |
| 5,762,541 A | 6/1998 | Heath et al. |
| 5,775,902 A | 7/1998 | Matsutani et al. |
| 5,788,488 A | 8/1998 | Grossman |
| 5,788,497 A | 8/1998 | Chalifoux |
| 5,791,902 A | 8/1998 | Lauks |
| 5,803,732 A | 9/1998 | Musikant et al. |
| 5,807,106 A | 9/1998 | Heath |
| 5,823,774 A | 10/1998 | Abbott et al. |
| 5,833,457 A * | 11/1998 | Johnson ............ 433/81 |
| 5,833,693 A | 11/1998 | Abrahami |
| 5,836,764 A | 11/1998 | Buchanan |
| 5,842,861 A | 12/1998 | Buchanan |
| 5,842,862 A | 12/1998 | Nissan |
| 5,855,479 A | 1/1999 | Wong et al. |
| 5,857,852 A | 1/1999 | Garman |
| 5,873,515 A | 2/1999 | Dunn et al. |
| 5,882,198 A | 3/1999 | Taylor et al. |
| 5,897,316 A | 4/1999 | Buchanan |
| 5,904,480 A | 5/1999 | Farzin-Nia et al. |
| 5,904,679 A | 5/1999 | Clayman |
| 5,912,775 A | 6/1999 | Glockler |
| 5,915,964 A | 6/1999 | Walia |
| 5,939,440 A | 8/1999 | Dykstra et al. |
| 5,941,700 A | 8/1999 | Fuchs |
| 5,947,730 A | 9/1999 | Kaldestad |
| 5,980,250 A | 11/1999 | McSpadden |
| 6,015,292 A | 1/2000 | Euvrard et al. |
| 6,042,375 A | 3/2000 | Riitano |
| 6,042,376 A * | 3/2000 | Cohen et al. ............ 433/102 |
| 6,053,735 A | 4/2000 | Buchanan |
| 6,068,642 A | 5/2000 | Johnson et al. |
| 6,074,209 A | 6/2000 | Johnson |
| 6,106,296 A | 8/2000 | Johnson |
| 6,113,392 A | 9/2000 | Braun |
| 6,126,521 A | 10/2000 | Shearer et al. |
| 6,128,966 A | 10/2000 | Usui et al. |
| 6,149,501 A | 11/2000 | Farzin-Nia et al. |
| 6,155,821 A | 12/2000 | Hellum |
| 6,174,165 B1 | 1/2001 | Katsuumi et al. |
| 6,179,617 B1 | 1/2001 | Ruddle |
| 6,206,695 B1 | 3/2001 | Wong et al. |
| 6,217,335 B1 | 4/2001 | Riitano et al. |
| 6,228,491 B1 | 5/2001 | Antelman |
| 6,231,340 B1 | 5/2001 | Kildea, Jr. |
| 6,257,089 B1 | 7/2001 | Hashimoto et al. |
| 6,258,102 B1 | 7/2001 | Pagedas |
| 6,273,714 B1 | 8/2001 | Farzin-Nia et al. |
| 6,293,794 B1 | 9/2001 | McSpadden |
| 6,299,445 B1 | 10/2001 | Garman |
| 6,315,557 B1 | 11/2001 | Messick |
| 6,315,558 B1 | 11/2001 | Farzin-Nia et al. |
| 6,375,450 B1 | 4/2002 | Golomb et al. |
| 6,379,155 B1 | 4/2002 | Riitano et al. |
| 6,382,973 B2 | 5/2002 | Murai et al. |
| 6,390,013 B1 | 5/2002 | Cornell |
| 6,390,019 B1 | 5/2002 | Grimbergen et al. |
| 6,409,506 B1 | 6/2002 | Graybill |
| 6,419,488 B1 | 7/2002 | McSpadden et al. |
| 6,428,317 B1 | 8/2002 | Abel |
| 6,428,634 B1 | 8/2002 | Besselink et al. |
| 6,431,860 B1 | 8/2002 | Aono et al. |
| 6,443,730 B2 | 9/2002 | Davidson |
| 6,460,079 B1 | 10/2002 | Blumenau |
| 7,942,673 B2 * | 5/2011 | Buchanan ............ 433/224 |
| 7,967,605 B2 * | 6/2011 | Goodis ............ 433/102 |
| 2002/0090594 A1 | 7/2002 | Riitano et al. |
| 2004/0115589 A1 * | 6/2004 | Karmaker et al. ............ 433/81 |
| 2004/0265783 A1 * | 12/2004 | Karmaker et al. ............ 433/220 |
| 2005/0003328 A1 * | 1/2005 | Karmaker et al. ............ 433/220 |
| 2011/0129793 A1 * | 6/2011 | Goodis ............ 433/81 |

FOREIGN PATENT DOCUMENTS

| | | |
|---|---|---|
| CH | 0 657 981 | 10/1986 |
| EP | 0 402 293 | 12/1990 |
| EP | 0 780 100 | 7/2002 |
| WO | WO 02/062251 | 8/2002 |
| WO | WO 2004/034920 | 4/2004 |

OTHER PUBLICATIONS

Drake, S. et al., "Mechanical properties of orthodontic wires in tension, bending, and torsion," American Journal of Orthodontics 82(3): 206-210 (Sep. 1982).

Khier, S. et al., "Bending properties of superelastic and nonsuperelastic nickel-titanium orthodontic wires," American Journal of Orthodontics and Dentofacial Orthopedics 99(4): 310-318 (Apr. 1991).

Marshall T.D. & Cooley, R.L., "Evaluation of the Max titanium alloy retentive pins," American Journal of Dentistry 2(6): 349-353 (Dec. 1989).

Maslov, A.M., [Experience with the use of an endodontic drill bit], Stomatologiia 62(1): 25 (Jan.-Feb. 1983).

Mohlin, B. et al., "Examination of Chinese NiTi wire by a combined clinical and laboratory approach," 13(5): 386-391 (1991).

Möllersten, L., "Machinability of some dentin simulating materials," Swed. Dent. J. 9(5): 219-224 (1985).

Paulsen, K., [Experiences with high-speed drill and grinding instruments in ENT surgical interventions], Z. Laryngol Rhinol Otol. 51(2): 91-102 (Feb. 1972).

Ring, M.E., "The development of the dental drill," Compendium 9(6): 518 (Jun. 1988).

Stannard, J. et al., "Comparative friction of orthodontic wires under dry and wet conditions," American Journal of Orthodontics 89(6): 485-491 (Jun. 1986).

Sunil, K. et al., "Effects of clinical recycling on mechanical properties of nickel-titanium alloy wires," American Journal of Orthodontics and Dentofacial Orthopedics 100(5): 428-435 (Nov. 1991).

Viazis, A.D., "Clinical applications of superelastic nickel titanium wires," Journal of Clinical Orthodontics 25(6): 370-374 (Jun. 1991).

(56) References Cited

OTHER PUBLICATIONS

Wajs, S. & Bak, Z., [Historical outline of the development of the dental drill], Prot. Stom., pp. 89-100 (1971).
Wiskott, H.W. & Schatz, J.P., [Preprosthetic orthodontics: technical aspects of mechanotherapy], Cahiers de Prothese 75: 91-101 (Sep. 1991).
Francke, O.C., [From the history of dentistry. Drills and drill instruments], Odontologiska Foreningens Tidskrift 31(4): 356-359 (1967).
Freund, E. et al., [The application of a dental drill drilling device], Zentralbl Chir. 97(15): 483-484 (Apr. 1972).
Holtkamp, P., [The development of the drilling machine], Funktionelles Labor/Verschiedenes pp. 507-509 (May 1981).
Webers, A., [Drilling machines, turbines, small motors], Dent. Dienst. 22(1): 19-20 (Jan. 1970).
American Machinist, "Will Creep-Feed Grinding Catch on?" 124(12): 106-108 (Dec. 1980).
L. Stephen Buchanan, "The Art of Endodontics: Files of Greater Taper," Dentistry Today, pp. 42-53 (Feb. 1996).
L. Stephen Buchanan, "One-Visit Endodontics: A New Model of Reality," Dentistry Today, pp. 36-43 (May 1996).
C. J. Burstone & A. J. Goldberg, "Beta Titanium: A new orthodontic alloy," American J. of Orthodontics 77(2): 121-132 (Feb. 1980).
S. Civjan, et al., "Potential Applications of Certain Nickel-Titanium (Nitinol) Alloys," Journal of Dental Research 54(1): 89-96 (1975).
K. B. Lewis & W. F. Schleicher, The Grinding Wheel—A Textbook of Modern Grinding Practice, pp. 382-382 (1976 $3^{rd}$ Ed.).
D. Stoeckel & W. Yu, "Superelastic Ni-Ti Wire," Wire Journal Int'l, pp. 45-50 (Mar. 1991).
RMI Taitanium Brochure, 28 pages (before Jan. 31, 1992).
H. Walia, et al., "An Initiative Investigation of the Bending and Torsional Properties of Nitinol Root Canals," Journal of Endodontics 14(7): 346-351 (Jul. 1988).

\* cited by examiner

| GRINDING TOLERANCE: +0.005 +0.035 | | | | | PROGRESS PITCH | | | SLEEVE LENGTH ±0.3 | TIP COLOR CODE RING | TAPER COLOR CODE RING & STEPPER | REF. GPAO |
|---|---|---|---|---|---|---|---|---|---|---|---|
| N° | A ØPTE | ØB | ØC | ØD | ØE ±0.015 | ON TIP | AT 12mm | AT 17mm | ØFILL | | | |
| 20 | 0.20 | 0.52 | 0.68 | 0.76 | 0.70 | 0.70 | 1.05 | 1.20 | 0.80 | 21–25 | YELLOW | GREEN | lg21:20337301 lg25:20337307 |
| 25 | 0.25 | 0.57 | 0.73 | 0.81 | | | | | | | RED | GREEN | lg21:20337301 lg25:20337307 |
| 30 | 0.30 | 0.62 | 0.78 | 0.86 | | 0.87 | 1.10 | 1.5 | 1.00 | | BLUE | GREEN | lg21:20337301 lg25:20337307 |
| GRINDING TOLERANCE AFTER VIBRATING: ±0.015 | | | | | | | | | | | DIC0415 | DIC0416 DIC0411 | |

TABLE 2

| N° | GRINDING TOLERANCE | +0.005 | | +0.035 | | PROGRESS PITCH | | | SLEEVE LENGTH ±0.3 | TIP COLOR CODE RING | TAPER COLOR CODE RING & STEPPER | REF. GPAO |
|---|---|---|---|---|---|---|---|---|---|---|---|---|
| | ØA | ØB | ØC | ØD | ØE ±0.015 | ON TIP | AT 12mm | AT 17mm | ØFILL | | | |
| 30 | 0.30 | 0.70 | 0.90 | 0.98 | 0.80 | 1 | 1.52 | 1.75 | 1.00 | 21-25 | BLUE | BLACK | lg21:20337301 lg25:20337307 |
| | | | | | | | | | | | DIC0415 | DIC0416 DIC0411 | |
| GRINDING TOLERANCE AFTER VIBRATING: ±0.015 | | | | | | | | | | | | |

TABLE 3

| N° | ØA | ØB | ØC | ØD | ØE ±0.015 | PROGRESS PITCH | | | SLEEVE LENGTH ±0.3 | TIP COLOR CODE RING | TAPER COLOR CODE RING & STEPPER | REF. GPAO |
|---|---|---|---|---|---|---|---|---|---|---|---|---|
| | | | | | | ON TIP | AT 12mm | AT 17mm ØFILL | | | | |
| 20 | 0.20 | 0.44 | 0.56 | 0.64 | 0.60 | 0.57 | 0.87 | 0.80 | 21–25 | YELLOW | WHITE | lg21:20337301 lg25:20337307 |
| 25 | 0.25 | 0.49 | 0.61 | 0.69 | | | | | | RED | | lg21:20337301 lg25:20337307 |
| GRINDING TOLERANCE: +0.005 +0.035 | | | | | | | | | | DIC0415 | DIC0416 DIC0411 | |
| GRINDING TOLERANCE AFTER VIBRATING: ±0.015 | | | | | | | | | | | | |

TABLE 1

ENDODONTIC FILES AND OBTURATOR DEVICES AND METHODS OF MANUFACTURING SAME

RELATED APPLICATIONS

This application is a divisional application of U.S. patent application Ser. No. 11/081,974, filed on Mar. 16, 2005, now U.S. Pat. No. 7,967,605 which claims the benefit of U.S. Provisional Patent Application No. 60/553,792, filed Mar. 16, 2004 U.S. Provisional Patent Application No. 60/648,099, filed Jan. 28, 2005 and U.S. Provisional Patent Application No. 60/648,167 filed Jan. 28, 2005. Further, each of U.S. patent application Ser. No. 11/081,974, U.S. Provisional Patent Application No. 60/553,792, U.S. Provisional Patent Application No. 60/648,099, and U.S. Provisional Patent Application No. 60/648,167 is hereby incorporated in its entirety by reference thereto.

FIELD OF THE INVENTION

The present invention relates to endodontic files or drill bits, to endodontic obturator devices and to methods of manufacturing same, particularly, for the performance of root canal surgery.

BACKGROUND

The performance of root canal surgery is very common in the field of endodontics. One step that is performed during root canal surgery is removing tissue from the canal of the root of a patient's tooth. While various different methods, using various different endodontic files, are conventionally employed, typically a series of progressively larger and/or differently shaped files or drill bits (for the purposes of this application, the terms "file and "drill bit" shall be used interchangeably) are successively employed by an endodontist until a satisfactory amount of tissue has been removed from the canal of the root of the tooth.

There are many different types of endodontic files that are known in the art or that are currently in the market. However, none of these endodontic files, either when used separately or in combination with each other, perform satisfactorily. For instance, one of the problems experienced by conventional endodontic files is that cutting edges disposed on helical flutes of the endodontic files provide less than satisfactory removal of tissue from the canal of the root of the tooth. Thus, when used in certain portions of the canal of the root of a tooth, the files do not adequately remove tissue that is desired to be removed.

Furthermore, another problem that is experienced by conventional endodontic files is that they are prone to break during use. As conventional endodontic files are rotated within the canal of the root of a tooth, friction occurs between the outer diameter of the file and the inner wall of the canal of the root, causing the file to experience torque forces. The frictional forces are especially experienced by endodontic files because endodontic files are employed in canal of the roots of teeth, which are uneven in shape and may curve significantly in several directions. Furthermore, these frictional forces are exacerbated when tissue becomes clogged within the helical flutes and tissue is unable to be moved out of the root canal, causing the file to experience still further torque forces. These torque forces, if sufficiently large, may cause the file to break in the canal of the root. When a file breaks within an canal of the root, extracting the broken file therefrom may be very problematic.

Still further, another problem that is experienced by conventional endodontic files is that they remove not merely tissue in the canal of the root that is desired to be removed, but in some instances, portions of the inner wall of the canal of the root that are not desired to be removed. Because of the uneven shape and significant curvature of the canal of the root, conventional endodontic files—by virtue of their limited flexibility—may be pressed against, and thereby cut into, certain portions of the inner walls of the canal of the root more severely than desired, resulting in the undesired removal of the inner walls of the canal of the root in these portions. It is typically a goal when performing root canal surgery to minimize the removal of the inner wall of the canal of the root.

Another step during, e.g., root canal procedures, is to obturate or fill the void in the canal after the tissue is removed. Conventional obturator devices typically employ a constant taper. It is found that most canals of roots do not have a constant taper and thus conventional obturator instruments bind at the top of the canal. Also, conventional obturator devices typically have a conical or circle cross-section. This does not allow the flow of excess filler material to move out of the canal and instead pushes the excess filler material out the canal and into the body.

Thus, there is a need for an endodontic file, or a series of endodontic files, that perform satisfactorily when used during an endodontic surgical procedure such as a root canal procedure. There is also a need for an endodontic obturator device, or a series of endodontic obturator devices, that enable a root canal to be filled after an endodontic surgical procedure, such as a root canal procedure, has been performed using an endodontic file, or a series of endodontic files, of the present invention.

SUMMARY

The present invention, according to the various embodiments described hereinbelow, may relate to an endodontic file, a set of endodontic files, a method of manufacturing an endodontic file and a method of manufacturing a set of endodontic files. It should be understood that the present invention is intended to cover each of these aspects. For instance, in accordance with various embodiments, the present invention relates to an endodontic file, a set of endodontic files, a method of manufacturing an endodontic file and a method of manufacturing a set of endodontic files wherein the endodontic file(s) or the manufacturing the file(s) may include or involve features corresponding to the clearance angle of same.

For example, the endodontic file(s) of the present invention, such as those manufactured in accordance with the methods of the present invention, may comprise:

1) A file body extending from a tip region to a shank region;

2) At least one helical flute extending along at least a portion of the file;

3) the at least one helical flute having an up-sharp cutting edge without a land, wherein the cutting edge defines a non-negative clearance angle and/or wherein the cutting edge defines a clearance angle less than 35 degrees;

4) wherein the clearance angle of a single file, or in the case of a set at least one file, may vary between the tip region and the shank region and/or is less than 35 degrees; and 5) wherein the clearance angle may be formed by a flat relief and/or a radial relief.

In one embodiment, the series or set of endodontic files has at least two files with the same tip diameter. In one embodiment, the series or set of endodontic files has at least two files with tip diameters that are within 0.025 mm of each other, said dimension being considered to be the same tip diameter. In one embodiment, the series or set of endodontic files has at least two files without the same tip diameter.

In one embodiment, the series or set of endodontic files has at least two files with the same taper. In one embodiment, the series or set of endodontic files has at least two file with tapers at similar portions of the file that are within 0.01 mm/mm of each other, said dimension being considered to be the same taper. In one embodiment, the series or set of endodontic files has at least two files without the same taper.

In various embodiments, the present invention includes features corresponding to the cutting edges of the endodontic files. For instance, along at least a portion of a cutting edge of at least one flute, the clearance angle may be one of <35 degrees, <25 degrees, <15 degrees and <5 degrees. For each, may be constant or may vary in the direction from tip to shank. In one embodiment, the clearance angle is 0 degrees and varies in the direction from tip to shank. In one embodiment, the file has a land and varies in the direction from tip to shank.
The clearance angle may vary linearly or non-linearly along at least a portion of a cutting edge of at least one flute. The clearance angle may vary in equal or unequal portions along at least a portion of a cutting edge of at least one flute. The clearance angle may increase in the direction from tip to shank. Alternatively, the clearance angle may decrease in the direction from tip to shank. For instance, the clearance angle may decreases linearly or non-linearly along at least a portion of a cutting edge of at least one flute. The clearance angle may decrease in equal or unequal portions along at least a portion of a cutting edge of at least one flute. In one embodiment, the clearance angles of the cutting edge(s) of one or more flutes along at least a portion of the file may be different from the other flutes at that specific portion of the file.

In one embodiment, at least one of the cutting edges of one of the flutes may have a land, while at least one of the cutting edges of one of the other flutes may not have a land or may have an up-sharp edge. In one embodiment, at least one of the cutting edges may have a land at some point and at another point that same cutting edge may not have a land or may have an up-sharp edge. In one embodiment, at least a portion of the clearance angle of at least one of the cutting edges of one of the flutes is formed by a flat relief which forms an up-sharp edge and the length of the flat relief is <75%, <50%, <40%, <30%, <20%, <10%, or <5% of the outside diameter of the file at that longitudinal location of the file.

In one embodiment, at least a portion of the clearance angle of at least one of the cutting edges of one of the flutes is formed by a radial relief which forms an up-sharp edge and the length of the radial relief is <75%, <50%, <40%, <30%, <20%, <10%, or <5% of the outside diameter of the file at that longitudinal location of the file.

In accordance with various other embodiments, the present invention relates to an endodontic file, a set of endodontic files, a method of manufacturing an endodontic file and a method of manufacturing a set of endodontic files wherein the endodontic file(s) or the manufacturing the file(s) may include or involve features corresponding to the file body taper of same.

For example, the endodontic file(s) of the present invention, such as those manufactured in accordance with the methods of the present invention, may comprise:

1) A file body extending from a tip region to a shank region;

2) the file body defining a taper, wherein a rate of taper along at least a portion of the file body from the tip region towards the shank region varies from another portion of the file body and/or wherein a rate of taper along at least a portion of the file body decreases from another portion from the tip region towards the shank region and/or wherein a rate of taper along at least a portion of the file body increases from another portion from the tip region towards the shank region;

3) wherein the cutting edge has an up-sharp cutting edge without a land and/or wherein the cutting edge has a land and/or wherein at least one cutting edge of a flute has a land and at least one cutting edge of another flute has an up-sharp edge; and 4) wherein at least one of the above-described characteristics occurs in a single file and/or at least a single file or more in a set.

In one embodiment, the series or set of endodontic files has at least two files with the same tip diameter. In one embodiment, the series or set of endodontic files has at least two files with tip diameters that are within 0.025 mm of each other that will be considered to be the same tip diameter. In one embodiment, the series or set of endodontic files has at least two files without the same tip diameter.

In one embodiment, the series or set of endodontic files has at least two files with the same taper. In one embodiment, the series or set of endodontic files has at least two files with tapers at similar portions of the file that are within 0.01 mm/mm of each other that will be considered to be the same taper. In one embodiment, the series or set of endodontic files has at least two files without the same taper.

In various embodiments, the present invention includes features of the file taper body. For instance, along at least a portion of the file body, or in a set along at least a portion of a file body of at least one file, the rate of taper along a least a portion of the file body may decrease linearly or non-linearly between the tip region and the shank region. The rate of taper along the entire file body may decreases linearly or non-linearly from the tip region towards the shank region.

In one embodiment, the rate of taper at the tip region is less than 0.07 mm/mm. The rate of taper of at least a portion of, or of the entire, file body decreases thereafter. In one embodiment, the rate of taper at the tip region is less than 0.09 mm/mm. The rate of taper of at least a portion of, or of the entire, file body decreases thereafter. In one embodiment, the file body includes two or more longitudinal portions. The at least two longitudinal portions may be of equal or unequal length. In one embodiment, the file body includes three or more longitudinal portions. The at least two longitudinal portions may be of equal or unequal length. In one embodiment, the three or more longitudinal portions may have two or more portions of equal length. In one embodiment, the three or more longitudinal portion may have two or more portions of unequal length.

In various embodiments of the present invention, the working length of the file body may be 25 mm or less, 16 mm or less, 13 mm or less or 4 mm or more. In one embodiment, a longitudinal portion of the working length has a rate of taper of 0.04 mm/mm or less. A second longitudinal portion of the working length may have a rate of taper of 0.04 mm/mm or less which is smaller than the previous portion. The longitudinal portion of the working length may have a rate of taper at the tip of 0.04 mm/mm or less. A second longitudinal portion of the working length may have a rate of taper of 0.04 mm/mm or less which is smaller than the previous portion. In one embodiment, the longitudinal portions of the working lengths have rates of taper of 0.04 mm/mm, 0.03 mm/mm, and 0.02 mm/mm, where the rates of taper start at, e.g., the tip.

In one embodiment, a longitudinal portion of the working length has a rate of taper of 0.06 mm/mm or less. A second longitudinal portion of the working length may have a rate of taper of 0.06 mm/mm or less which is smaller than the previous portion. A longitudinal portion of the working length may have a rate of taper at the tip of 0.06 mm/mm or less. The second longitudinal portion of the working length may have a rate of taper of 0.06 mm/mm or less which is smaller than the previous portion. In one embodiment, the longitudinal portions of the working lengths have rates of taper of 0.06 mm/mm, 0.04 mm/mm, and 0.02 mm/mm, respectively, where the rates of taper start, e.g., at the tip.

In one embodiment, a longitudinal portion of the working length has a rate of taper of 0.08 mm/mm or less. A second longitudinal portion of the working length may have a rate of taper of 0.08 mm/mm or less which is smaller than the previous portion. The longitudinal portion of the working length may have a rate of taper at the tip of 0.08 mm/mm or less. The second longitudinal portion of the working length may have a rate of taper of 0.08 mm/mm or less which is smaller than the previous portion. In one embodiment, the longitudinal portions of the working lengths have rates of taper of 0.08 mm/mm, 0.04 mm/mm, and 0.02 mm/mm, respectively, where the rates of taper start, e.g., at the tip.

In one embodiment, a longitudinal portion of the working length has a rate of taper of 0.10 mm/mm or less. A second longitudinal portion of the working length may have a rate of taper of 0.10 mm/mm or less which is smaller than the previous portion. The longitudinal portion of the working length may have a rate of taper at the tip of 0.10 mm/mm or less. The second longitudinal portion of the working length may have a rate of taper of 0.10 mm/mm or less which is smaller than the previous portion. The longitudinal portions of the working lengths may have rates of taper of 0.10 mm/mm, 0.05 mm/mm, and 0.02 mm/mm, where the rates of taper start at, e.g., the tip.

In one embodiment, a longitudinal portion of the working length has a rate of taper of 0.12 mm/mm or less. A second longitudinal portion of the working length may have a rate of taper of 0.12 mm/mm or less which is smaller than the previous portion. The longitudinal portion of the working length may have a rate of taper at the tip of 0.12 mm/mm or less. The second longitudinal portion of the working length may have a rate of taper of 0.12 mm/mm or less which is smaller than the previous portion. The longitudinal portions of the working lengths may have rates of taper of 0.12 mm/mm, 0.06 mm/mm, and 0.02 mm/mm, where the rates of taper start at, e.g., the tip.

In one embodiment, a longitudinal portion of the working length has a rate of taper of 0.20 mm/mm or less. A second longitudinal portion of the working length may have a rate of taper of 0.20 mm/mm or less which is smaller than the previous portion. The longitudinal portion of the working length may have a rate of taper at the tip of 0.20 mm/mm or less. The second longitudinal portion of the working length may have a rate of taper of 0.20 mm/mm or less which is smaller than the previous portion. The longitudinal portions of the working lengths may have rates of taper of 0.20 mm/mm, 0.10 mm/mm, and 0.05 mm/mm, where the rates of taper start at, e.g., the tip.

In one embodiment, a rate of taper for one of the longitudinal portions of the working length differs from a rate of taper for another of the longitudinal portions of the working length by at least 0.01 mm/mm, 0.02 mm/mm, 0.03 mm/mm or 0.04 mm/mm.

In one embodiment, the file body has at least three (3) different portions of rates of taper along the length of the file where the 2nd portion is in a decreasing rate of taper compared to the adjacent 1st portion. The 2nd portion may be decreasing at a constant or non-constant rate of taper and at multiple different decreasing rates of taper. The 3rd portion is at an increasing rate of taper compared to the adjacent 2nd portion.

In one embodiment, the file body has at least three (3) different portions of rates of taper along the length of the file where the 2nd portion is in an increasing rate of taper compared to the adjacent 1st portion. The 2nd portion may be increasing at a constant or non-constant rate of taper and at multiple different increasing rates of taper. The 3rd portion is at a decreasing rate of taper compared to the adjacent 2nd portion.

The present invention, according to various embodiments thereof, also relates to a method of manufacturing an endodontic file and/or an endodontic file in a series, the endodontic file including a file body extending over at least a portion of the file, the method including the step of performing a process so as to form at least two helical flutes in the file body, the at least two helical flutes extending over at least a portion of the file, at least two cutting edges being formed, wherein the process forms in a rake angle-forming step a rake angle of the cutting edges, and forms in a clearance angle-forming step a clearance angle of another cutting edge.

In one embodiment, the clearance angle of one cutting edge formed in the clearance angle-forming step is less than one of 45°, 40, 30°, 20°, or 10°. In one embodiment, the process is a grinding process. In one embodiment, the clearance angle of all of the flutes may be identical or different along a portion of the length of the file.

The present invention, according to various embodiments thereof, also relates to a method of manufacturing an endodontic file and/or an endodontic file in a series, the endodontic file including a file body extending over at least a portion of the file, the method including the step of performing a process so as to form at least two helical flutes in the file body, the at least two helical flutes extending over at least a portion of the file, at least two cutting edges being formed, wherein the process forms in a rake angle-forming step a rake angle of the cutting edges, and forms in a clearance angle-forming step a clearance angle of another cutting edge, wherein the rake angle of one of the cutting edges is not formed in the same step as a clearance angle of another cutting edge, and the clearance angle of the other cutting edge is not formed in the same step as the rake angle of the other one of the cutting edges. In one embodiment, the process is a grinding process.

The present invention, according to various embodiments thereof, relates to a method of manufacturing an endodontic file, the endodontic file including a file body extending from a tip region to a shank region, the method including the steps of performing a process so as to form at least two helical flutes in the file body, the at least two helical flutes extending from the tip region towards the shank region, at least two cutting edges being formed between adjacent helical flutes, wherein the process forms in a rake angle-forming step a non-negative rake angle of a first one of the cutting edges, and forms in a clearance angle-forming step a clearance angle of an adjacent cutting edge. In one embodiment, the first process is a grinding process. In one embodiment, the second process is a grinding process.

The present invention, according to the other embodiments described hereinbelow, relates to an endodontic obturator device, a set of endodontic obturator devices, a method of manufacturing an endodontic obturator device and a method of manufacturing a set of endodontic obturator devices. It should be understood that the present invention is intended to cover each of these aspects. For instance, in accordance with various embodiments, the present invention relates to an endodontic obturator device, a set of endodontic obturator devices, a method of manufacturing an endodontic obturator device and a method of manufacturing a set of endodontic obturator devices wherein the endodontic obturator device(s) or of manufacturing the obturator device(s) may include one or more of the features described hereinbelow.

For example, the endodontic obturator device(s) of the present invention, such as those manufactured in accordance with the methods of the present invention, may include at least a portion extending from a tip region to a shank region; and a body defining a taper, wherein a rate of taper along at least a portion of the body relative to another portion from the tip region towards the shank region, may be one, one or more, or all of a) variable; b) non-constant; c) decreasing; d) increasing; and e) zero taper. According to some embodiments of the present invention, the obturators of the present invention may have any or all of the taper arrangements described herein above in connection with the endodontic files, thereby ensuring that the openings formed by the endodontic files have a corresponding instrument for putting material, e.g., gutta percha or the like, back into the opening. In one embodiment, the obturator has an ovoid cross-section for at least a portion of the longitudinal length of the obturator.

For a series or set of endodontic obturator devices, as used hereinabove, the series or set of the device may have at least two with the same tip diameter. In one embodiment, the series or set of the device may have at least two with tip diameters that are within 0.025 mm of each other that will be considered to be the same tip diameter. In one embodiment, the series or set of the device may have at least two without the same tip diameter.

In one embodiment, the series or set of the device may have at least two with the same taper. The series or set of the device may have at least two with tapers at similar portions that are within 0.01 mm/mm of each other that will be considered to be the same taper. The series or set of the device may have at least two without the same taper.

The term "device" as used hereinabove may be defined as, for instance, a cone, appliance, or carrier. It may be made of gutta-percha, polymer, rubber, resin, metal, or other material and may be used to fill a root canal space whether alone or covered with a material. The device may be a single unit or multiple units, may have a handle, attached or unattached, as one unit or multiple separate units, made of similar or dissimilar materials or configurations. Also, it may have length indicator markings, grooves, a smooth surface and/or homogeneous or multiple layers of multiple or single materials being at least one form of gutta-percha, polymer, metal, or other material.

In various embodiments, the present invention includes features corresponding to the body of the endodontic obturator device. For instance, the present invention may include features wherein along at least a portion of the endodontic obturator device, the rate of taper along at least a portion of the device body decreases linearly between the tip region and the shank region, the rate of taper along at least a portion of the body decreases non-linearly between the tip region and the shank region. Also, the rate of taper along the entire body may decrease either linearly or non-linearly from the tip region towards the shank region.

In one embodiment, the body has at least three (3) different portions of rates of taper along the body where the 2nd portion is in a decreasing rate of taper compared to the adjacent 1st portion. The 2nd portion may be decreasing at a constant or non-constant rate of taper and at multiple different decreasing rates of taper. The 3rd portion is at an increasing rate of taper compared to the adjacent 2nd portion.

In another embodiment, the body has at least three (3) different portions of rates of taper along the body where the 2nd portion is in an increasing rate of taper compared to the adjacent 1st portion. The 2nd portion may be increasing at a constant or non-constant rate of taper and at multiple different increasing rates of taper. The 3rd portion is at a decreasing rate of taper compared to the adjacent 2nd portion.

Furthermore, the present invention, according to the various embodiments described hereinbelow, relates to one or more endodontic files, which may together form a set of endodontic files. In one embodiment, the endodontic file includes a working length having at least one cutting edge configured to remove tissue from the root canal of a tooth. The endodontic file also includes a shank portion located proximally relative to the working length, the shank portion having an outer diameter that is smaller than the outer diameter of at least one portion of the working length. Preferably, the shank portion has an outer diameter that is smaller than the outer diameter of a portion of the working length that is immediately adjacent to the shank portion. The reduced outer diameter dimension of the shank portion enables tissue that has been removed from the root canal of a tooth to more easily travel upwardly and out of the canal while the endodontic file is being used, since the reduced diameter provides additional space for the tissue to travel within.

Advantageously, the working length includes three working length portions. For one configuration of files, the three working length portions have respective rates of taper of 6%, 3% and 2%. For a second configuration of files, the three working length portions have respective rates of taper of 8%, 4% and 2%. For a third configuration of files, the three working length portions have respective rates of taper of 10%, 5% and 2%.

The shank portion may include a first shank portion and a second shank portion, the first shank portion being located distally relative to the second shank portion. In some embodiments, the second shank portion has an outer diameter dimension that is larger than the first shank portion, and may be the dimension of the blank that is used to form the file during the forming procedure. The second shank portion may include a shank mating arrangement configured to mate with a complementary tool, e.g., a hand-drill or a powered endodontic drill. The shank mating arrangement may be integrally formed with the second shank portion, or else may be separately formed from, and subsequently mounted on, the second shank portion. Likewise, the first shank portion may include a stopper ring, which is either integrally formed with the first shank portion or separately formed from, and subsequently mounted on, the first shank portion.

The endodontic file may be configured such that the outer diameter of the shank portion steps down to the reduced shank dimension. Alternatively or additionally, the endodontic file may be configured such that the outer diameter of the shank portion tapers down to the reduced shank dimension. In one embodiment, at least one of the first and second files is comprised of a nickel titanium alloy. Furthermore, at least one of the first and second files may be comprised of a nickel titanium alloy containing at least 70% titanium. Furthermore, at least one of the first and second files may be comprised of stainless steel. Still further, at least one of the first and second files is comprised of polymer.

DETAILED DESCRIPTION

The present invention, according to various embodiments thereof, relates to an endodontic file that may be employed in a dental or surgical procedure, for instance an endodontic surgical procedure like a root canal surgery. In another embodiment, the present invention relates to a series of endodontic files that may be successively employed in an endodontic surgical procedure. For the purposes of example only, the present invention will be described hereinafter in connection with an endodontic file or a series of endodontic files that are suitable for use in an endodontic surgical procedure. However, it should be recognized that the present invention, in accordance with other embodiments thereof, may also be used for other types of dental or surgical procedures.

Figure 1:
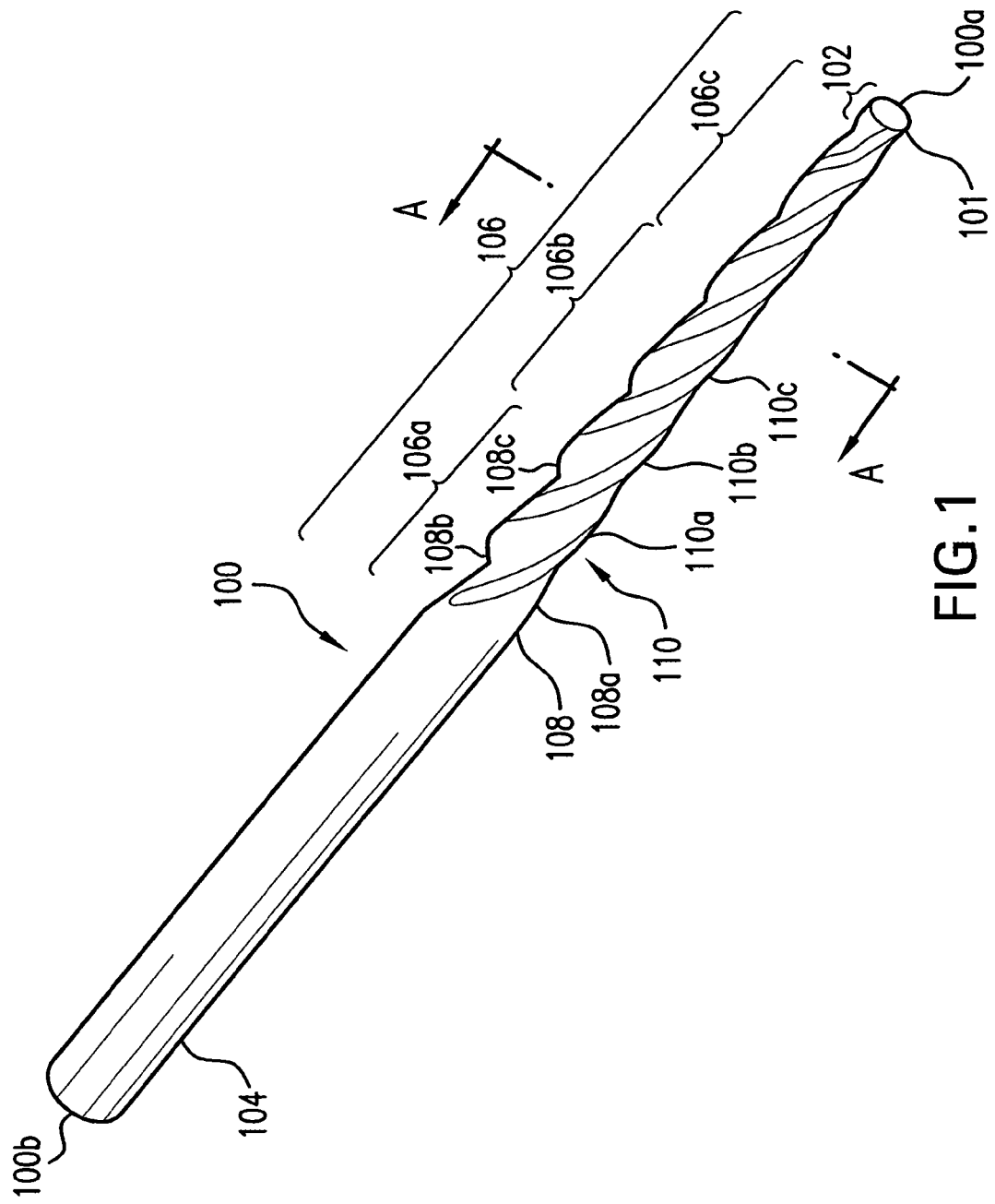
FIG. 1 is a perspective view of an endodontic file, according to one example embodiment of the present invention.

FIG. 1 illustrates an endodontic file 100 according to one embodiment of the present invention. According to one embodiment of the present invention, each endodontic file 100 is formed from a nickel titanium alloy, commonly referred to as "nitinol". More specifically, the nitinol material from which each endodontic file 100 is formed has an A(f) temperature not less than −5° C. Advantageously, the nitinol material from which each endodontic file 100 is formed has an A(f) temperature which is preferably greater than 0° C., preferably greater than 5° C. greater than 10° C. and most preferably greater than 10° C. The A(f) temperature of the nitinol refers to the temperature at which the austenite transition phase of the nitinol starts. The austenite transition phase of the nitinol, which includes a range of approximately 50° C., is the range of temperatures within which the nitinol has the desired degree of elasticity and shape memory, thereby ensuring optimal performance during its use. Thus, in a preferred embodiment, the nitinol is configured to be in the austenite phase, and to thereby exhibit maximum shape memory and elasticity, when operated within a human body at temperatures of less than 50° C. and preferably between 37° C. to 50° C.

Generally, the following is a list of some of the features of the endodontic file 100:
100: total endodontic file;
100a: distal-most end of file;
100b: proximal-most end of file;
101: start of the tip or tip;
102: tip region (may be one of any tip configurations before the flutes start, and preferably is, e.g., a non-cutting or bullet nose tip that is absent of any cutting surfaces, edges, or flutes);
104: shank region, e.g., extends from proximal-most end of file 100b to the beginning of the working length 106;
106: working length, e.g., extends from tip region 102 to the start of shank region 104, working length portions 106a, 106b and 106c show, e.g., three portions of the working length;
108: flute, e.g., a region or space adjacent to a cutting edge; individual flutes 108a, 108b and 108c define each flute;
110: cutting edge, e.g., located adjacent to a flute and defined by a rake angle on one side of the cutting edge and a clearance angle on the opposite side of the cutting edge; cutting edges 110a, 110b and 110c define each cutting edge;
1101: rake angle;
1102: clearance angle;
120: outside diameter of the file; and
130: inside diameter of the file.

More specifically, each endodontic file 100 includes a tip 101 at the distal-most end 100a of the endodontic file 100. The tip 101 may be any type of drill tip but is preferably a non-cutting type of file tip. The use of a non-cutting type of file tip may help prevent the tip of the file from binding, particularly when the file tip is advanced sufficiently so as to emerge from the apex of the canal of the root. Each endodontic file 100 includes a shank 105 at the proximal-most end 100b of the endodontic file 100. The shank 105 may be any type of drill shank but preferably has a shape, when viewed in cross-section, that is configured to engage a complementary-shaped drill device for rotating the endodontic file 100, as set forth more fully below. An additional handle may be added over the shank to allow it to be gripped by a user's fingers or to be inserted into a drill or hand-piece.

Each endodontic file 100 also includes a working length 106 that extends from a tip region 102, which is adjacent to the tip 101, to a shank region 104, which is adjacent to the shank 105. The working length 106 includes at least one helical flute 108. In the embodiment shown in FIG. 1, the working length 106 of the endodontic file 100 includes three helical flutes 108a, 108b and 108c. Located between each pair of adjacent flutes and defined thereby is a respective cutting edge 110. For instance, located between adjacent flutes 108a and 108b and defined thereby is a cutting edge 110a. Likewise, located between adjacent flutes 108c and 108c and defined thereby is a cutting edge 110b, and located between adjacent flutes 108c and 108a and defined thereby is a cutting edge 110c.

Figure 2:
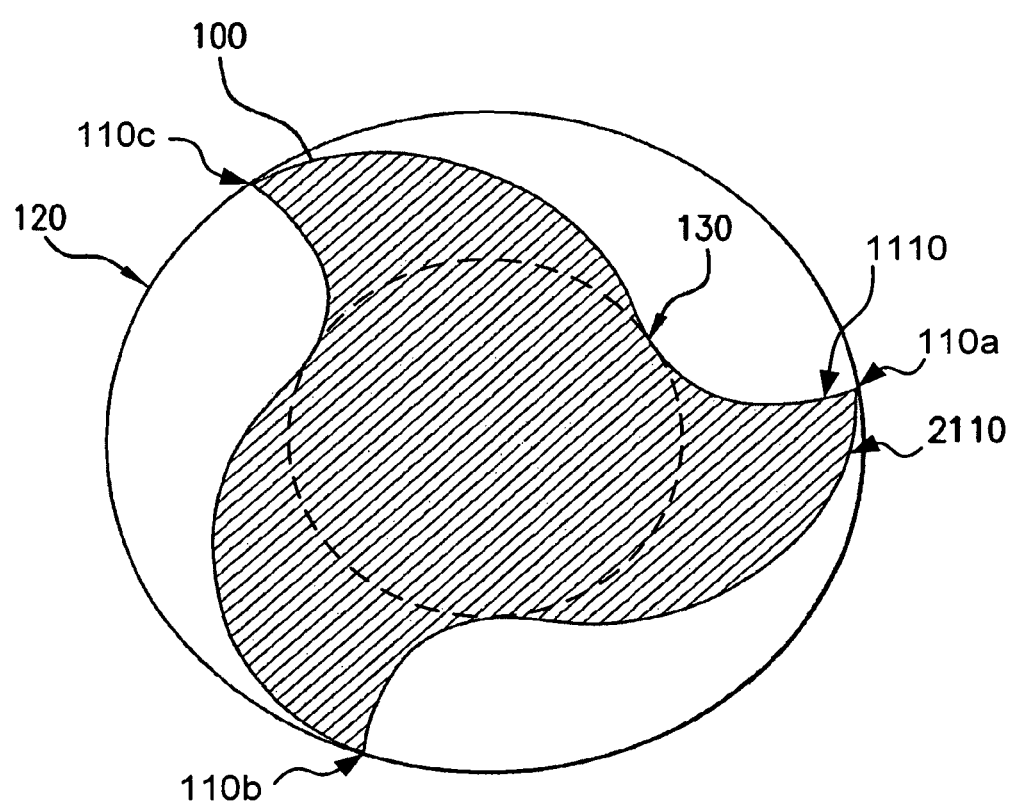
FIG. 2 is a cross-sectional view of the endodontic file illustrated in FIG. 1, taken along lines A-A.

FIG. 2 is a cross-sectional view of the endodontic file 100 illustrated in FIG. 1 taken along lines A-A. As shown in FIG.

2, the endodontic file 100 is arranged so that, when viewed in cross-section, the three helical flutes are circumferentially spaced around the endodontic file 100. In one embodiment, the endodontic file 100 is arranged so that, when viewed in cross-section, the three helical flutes are equally circumferentially spaced, e.g., such that the three helical flutes 108a, 108b and 108c, and consequently the three cutting edges 110a, 110b and 110c, are located 120 degrees apart from each other. However, in a preferred embodiment, the endodontic file 100 is arranged so that, when viewed in cross-section, the three helical flutes are not equally circumferentially spaced. In this preferred embodiment, the endodontic file 100 is arranged so that, when viewed in cross-section, the three helical flutes 108a, 108b and 108c, and consequently the three cutting edges 110a, 110b and 110c, are located approximately 112, 132 and 116 degrees apart from each other, respectively. Having the endodontic file 100 arranged so that, when viewed in cross-section, the three helical flutes 108a, 108b and 108c, and consequently the three cutting edges 110a, 110b and 110c, are not equally circumferentially spaced, for instance located approximately 112, 132 and 116 degrees apart from each other, respectively, may decrease the resonance that is experienced by the endodontic file 100 during operation.

At least a portion of one of the cutting edges 110a, 110b and 110c may be an "up-sharp" cutting edge. For the purposes of this application, the term "up-sharp" shall refer to a cutting edge that has substantially no land between adjacent flutes. In other words, and as shown in FIG. 2, the endodontic file 100, when viewed in cross-section, intersects at a single point, e.g., each cutting edge 110, a circle 120 that circumscribes all three cutting edges 110a, 110b and 110c.

Figure 4:
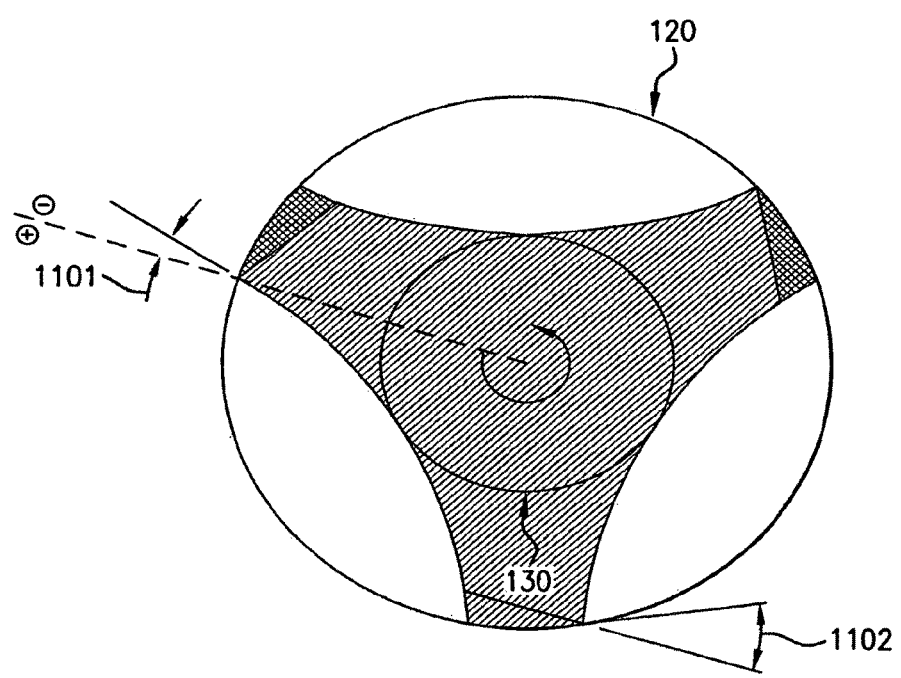
FIG. 4 is a cross-sectional view of an endodontic file for illustrating, e.g., the clearance angle, the rake angle, etc. of the endodontic file.

At least a portion of one of the cutting edges 110 is preferably formed so as to have, on a first side 1110 of the cutting edge 110, a non-negative rake angle. The rake angle 1101 is an angle between the first side 1110 of the cutting edge 110 and the radius of circle 120 as measured at the point where the cutting edge 110 meets the circle 120, as illustrated, e.g., in FIG. 4. In one embodiment, the first side 1110 of the cutting edge 110 defines a rake angle that is constant along the entire working length 106 of the endodontic file 100. For instance, the first side 1110 of the cutting edge 110 may define a rake angle of approximately 5 degrees along the entire working length 106 of the endodontic file 100. FIG. 2 illustrates that cutting edge 110a is formed so as to have, on a first side 1110 of the cutting edge 110a, a rake angle of approximately 5 degrees. A rake angle of approximately 5 degrees provides for improved cutting of tissue as compared to a neutral or negative rake angle.

In another embodiment, the first side 1110 of the cutting edge 110 defines a rake angle that is not constant along the entire working length 106 of the endodontic file 100. For instance, the first side 1110 of the cutting edge 110 may define a rake angle that increases from approximately 5 degrees, at the tip region 102 of the endodontic file 100 to approximately 20 degrees at the shank region 104 of the endodontic file 100. Alternatively, the first side 1110 of the cutting edge 110 may define a rake angle that increases from approximately 10 degrees at the tip region 102 of the endodontic file 100 to approximately 20 degrees at the shank region 104 of the endodontic file 100. Having a rake angle that increases from the tip region 102 of the endodontic file 100 to the shank region 104 of the endodontic file 100 may provide for increased cutting efficiency of the endodontic file 100 as the endodontic file 100 is gradually inserted into the canal of the root.

In addition, each cutting edge 110 is preferably formed so as to have a second side 2110 of the cutting edge 110 that immediately curves inwardly relative to the curve defined by the circle 120. For instance, FIG. 2 illustrates that cutting edge 110a is formed so as to have a second side 2110 of the cutting edge 110a that immediately curves inwardly relative to the curve defined by the circle 120. By virtue of the second side of each cutting edge 110 immediately curving inwardly relative to the curve defined by the circle 120, there is no land provided at each cutting edge 110. For instance, the second side of each cutting edge 110 immediately curves inwardly relative to the curve defined by the circle 120, such that the portion of the second side of the cutting edge that follows the curve defined by the circle 120 is no more than the approximate width of the cutting edge 110, e.g., approximately 0.06 mm in width. Consequently, because there is no land provided at each cutting edge 110, the endodontic file 100 may experience less friction during operation as compared to conventional files that provide lands at each cutting edge 110. A decrease in friction may thereby decrease the torque experienced by the endodontic file 100 and minimize the likelihood of the endodontic file 100 breaking during operation.

In one embodiment, at least a portion of the clearance angle of at least one of the cutting edges of one of the flutes is formed by a flat relief which forms an up-sharp edge and the length of the flat relief is <75%, <50%, <40%, <30%, <20%, <10%, or <5% of the outside diameter of the file at that longitudinal location of the file. In addition, in one embodiment, at least a portion of the clearance angle of at least one of the cutting edges of one of the flutes is formed by a radial relief which forms an up-sharp edge and the length of the radial relief is <75%, <50%, <40%, <30%, <20%, <10%, or <5% of the outside diameter of the file at that longitudinal location of the file.

Rather, each cutting edge 110 is preferably formed so as to have, on the second side 2110 of the cutting edge 110, a non-negative clearance angle. The clearance angle 1102 is an angle between the second side 2110 of the cutting edge 110 and a tangent to the circle 120 as measured at the point where the cutting edge 110 meets the circle 120, as illustrated, e.g., in FIG. 4. In one embodiment, the second side 2110 of the cutting edge 110 defines a clearance angle that is constant along the entire working length 106 of the endodontic file 100. FIG. 2 illustrates that cutting edge 110a is formed so as to have, on a second side 2110 of the cutting edge 110a, a clearance angle of approximately 10 degrees. Additional embodiments of the present invention relating to the clearance angle of the endodontic file(s) are set forth more fully above. A clearance angle according to the various embodiments set forth herein may provide for decreased friction during operation, decreased torque and a reduced likelihood of breakage as more fully set forth above. In another embodiment, the second side 2110 of the cutting edge 110 defines a clearance angle that is not constant along the entire working length 106 of the endodontic file 100.

The endodontic file 100 is tapered over at least a portion of the working length 106 so that an outer diameter of the endodontic file 100 at the tip region 102, e.g., the diameter of the circle 120 that circumscribes all three cutting edges 110a, 110b and 110c at the tip region 102, is smaller than an outer diameter of the endodontic file 100 at the shank region 102, e.g., the diameter of the circle 120 that circumscribes all three cutting edges 110a, 110b and 110c at the shank region 104. Additional embodiments of the present invention relating to the file body taper of the endodontic file(s) are set forth more fully above. A file body taper according to the various embodiments set forth herein may provide for decreased friction during operation, decreased torque and a reduced likelihood of breakage as more fully set forth above.

Figure 3:
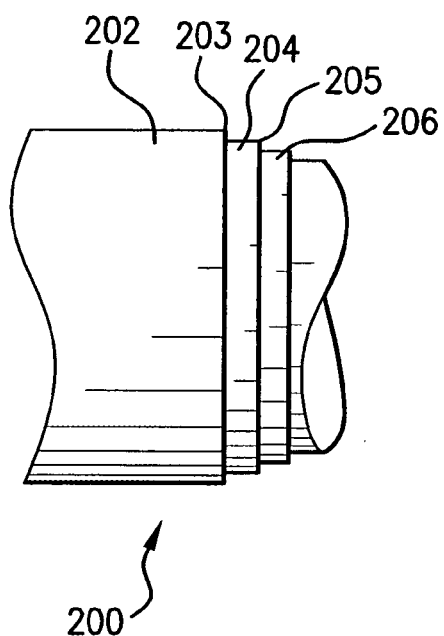
FIG. 3 is partial side view of an endodontic file, according to another example embodiment of the present invention.

In still other embodiments, the endodontic file 100 has a step design. More specifically, the endodontic file may be configured such that the diameter of the endodontic file has a plurality of separate axial regions wherein each axial region has a diameter that is larger than another axial region distally adjacent to the first axial region, and wherein the change in diameter between adjacent axial regions occurs abruptly, e.g., by a step. FIG. 3 illustrates a partial side view of an endodontic file 200 having a step design. As shown in FIG. 3, the endodontic file 200 has a first axial region 202, a second axial region 204, a third axial region 206, etc. The diameter of the first axial region 202 is larger than the diameter of the second axial region 204. The change in diameter between the first axial region 202 and the second axial region 204 occurs abruptly by step 203. Likewise, the diameter of the second axial region 202 is larger than the diameter of the third axial region 206. The change in diameter between the second axial region 204 and the third axial region 206 occurs abruptly by step 205. The step design of the endodontic file 200 may further reduce the friction that is experienced by the endodontic file 200 as compared to endodontic files having a diameter that tapers smoothly between the tip region and the shank region. It should be recognized that, while FIG. 3 illustrates some features of the endodontic file 200, for the purpose of clarity only, other features of the endodontic file 200, such as the helical flutes, cutting edges, etc. have not been shown in FIG. 3. The present invention contemplates that endodontic files having a step design may include some or all of the features and dimensions, e.g., rake angles, clearance angles, etc. disclosed herein in connection with endodontic files 100.

Each of the flutes 108 of the endodontic file 100 defines a flute pitch. The flute pitch is an angle between the cutting edge 110 of the flute 108 and a plane containing a central axis of the endodontic file 100. In one embodiment, the cutting edge 110 defines a flute pitch that is constant, e.g., 10 degrees, 25 degrees, etc., along the entire working length 106 of the endodontic file 100. In another embodiment, the cutting edge 110 defines a flute pitch that is not constant along the entire working length 106 of the endodontic file 100. For instance, the cutting edge 110 may define a flute pitch that increases from approximately 10 degrees at the tip region 102 of the endodontic file 100 to approximately 25 degrees at the shank region 104 of the endodontic file 100. Having a flute pitch that increases from the tip region 102 of the endodontic file 100 to the shank region 104 of the endodontic file 100 may provide for increased cutting efficiency of the endodontic file 100 as the endodontic file 100 is gradually inserted into the canal of the root. In those embodiments in which the cutting edge 110 defines a flute pitch that is not constant along the entire working length 106 of the endodontic file 100, the flute pitch may vary in either linear or non-linear fashion.

Each of the flutes 108 of the endodontic file 100 also defines a flute depth. The flute depth measures the deepest portion of the flute 108 and is expressed as a percentage equal to the measurement, taken along a radian of the circle 120 that circumscribes all three cutting edges 110a, 110b and 110c, of the deepest portion of the flute divided by the diameter of the circle 120. In one embodiment, the flute depth is constant along the entire working length 106 of the endodontic file 100. In another embodiment, the flute depth is not constant along the entire working length of the endodontic file 100. For instance, the flute depth may increase from approximately 15 percent at the tip region 102 of the endodontic file 100 to approximately 22 percent at the shank region 104 of the endodontic file 100. Alternatively, the flute depth may increase from approximately 20 percent at the tip region 102 of the endodontic file 100 to approximately 22 percent at the shank region 104 of the endodontic file 100. Having a flute depth that increases from the tip region 102 of the endodontic file 100 to the shank region 104 of the endodontic file 100 in the manner described hereinabove may provide space within the flutes 108 for the removal of additional tissue by the endodontic file 100 as the endodontic file 100 is gradually inserted into the canal of the root. In addition, having a flute depth that increases from the tip region 102 of the endodontic file 100 to the shank region 104 of the endodontic file 100 in the manner described hereinabove may also provide a sufficiently large file core, illustrated in FIG. 2 as a circle 130 that circumscribes the deepest point of each of the flutes 108a, 108b and 108c, so as to minimize or at least reduce the likelihood of the file breaking during operation. In those embodiments in which the flute depth is not constant along the entire working length 106 of the endodontic file 100, the flute pitch may vary in either linear or non-linear fashion.

The shank 105 of the endodontic file 100 is configured to attach to a drill device or the like. For instance, the shank 105 may be shaped, when viewed in cross-section, so as to fit into a complementary shaped opening in a drill device of the like. In one embodiment, the shank 105 may be formed from a material, e.g., brass, that is different from the material, e.g., nitinol, from which the endodontic file 100 is formed, and is attached to the endodontic file 100 after both the shank 105 and the endodontic file 100 have been separately formed. Preferably, however, the shank 105 is integrally formed with the endodontic file 100. When shank 105 is integrally formed with the endodontic file 100, the overall length of the endodontic file 100 may be shorter than conventional endodontic files that have a shank subsequently attached, thereby improving the comfort of a patient by reducing the distance that the patient is required to open his or her mouth during an operation.

Each endodontic file 100 of the series has a working length 106 such as set forth more fully above, although any length may be employed. The endodontic files 100 in the series may each be the same length or may be different lengths.

The series of endodontic files 100 may include endodontic files 100 having various different diameters, various different rates of taper, etc. For instance, in one embodiment, the series has three sets of endodontic files 100, each set having endodontic files 100 with ten different diameters at the tip region 102, or tip sizes. For the endodontic files 100 of each particular tip size, the series includes a group of three endodontic files 100 each having a different rate of taper. Thus, in this embodiment, the series includes thirty different endodontic files 100, some or all of which may be selectively employed by, e.g., an endodontist, to remove tissue from the canal of the root of a patient's tooth.

In one embodiment, the series includes endodontic files 100 having the following diameters at the tip region 102: 0.20 mm, 0.25 mm, 0.30 mm, 0.35 mm, 0.40 mm, 0.45 mm, 0.50 mm, 0.55 mm and 0.60 mm. It should be recognized that, while in one embodiment of the present invention in which the series includes endodontic files 100 having ten different tip sizes, the series may include endodontic files 100 having less than or more than ten different tip sizes. It should also be recognized that, while in one embodiment of the present invention the series includes endodontic files 100 having these specific tip sizes, the series may include endodontic files 100 having tip sizes different from those.

As stated above, for each of these tip diameters, the series may include endodontic files 100 having different rates of taper. For instance, in one embodiment, the series includes files having one or more longitudinal regions. The files preferably have three regions, but may have any number of said regions. The regions may be of equal or unequal length. In a first group, the rates of taper for each region are 0.04 mm/mm, 0.03 mm/mm and 0.02 mm/mm, respectively. Specifically, the first region, e.g., adjacent to the tip of the files, has a rate of taper of 0.04 mm/mm. The second region, e.g., located proximal to the first region, has a rate of taper of 0.03 mm/mm. The third region, e.g., adjacent to the shank of the files, has a rate of taper of 0.02 mm/mm. The series may includes, in a second group, files 100 having regions of equal length in which the rates of taper are 0.06 mm/mm, 0.04 mm/mm and 0.02 mm/mm, respectively. The series may also include, in a third group, files 100 having regions of equal length in which the rates of taper are 0.08 mm/mm, 0.04 mm/mm and 0.0 mm/mm, respectively. It should be recognized that, while one embodiment of the present invention of the series includes endodontic files 100 having three different rates of taper, the series may include endodontic files 100 having less than or more than three different rates of taper. It should also be recognized that, while in one embodiment of the present invention the series includes endodontic files 100 having the specific listed rates of taper, the series may include endodontic files 100 having different rates of taper from those. It should also be recognized that, while the endodontic files 100 may each have regions having a constant rate of taper over the length of the region, in other embodiments, one or more of the endodontic files 100 may have regions having a rate of taper that varies along the working length 106 of the endodontic file 100, as set forth more fully above.

In one embodiment of the present invention, for each group of endodontic files 100, the cutting edge 110 of the endodontic file 100 defines a rake angle that varies between the tip region 102 of the endodontic file 100 and the shank region 104 of the endodontic file 100. For instance, in one embodiment, each of a first group of endodontic file 100 has a rake angle that is 5 degrees at the tip region 102 of the endodontic file 100 and that increases to a rake angle of approximately 20 degrees at the shank region 104 of the endodontic file 100. In addition, each of a second group of endodontic file 100 has a rake angle that is 5 degrees at the tip region 102 of the endodontic file 100 and that increases to a rake angle of approximately 20 degrees at the shank region 104 of the endodontic file 100. Also, each of a third group of endodontic file 100 has a rake angle that is approximately 10 degrees at the tip region 102 of the endodontic file 100 and that increases to a rake angle of approximately 20 degrees at the shank region 104 of the endodontic file 100. It should be recognized that, while the rake angle of each endodontic file 100 of the series may vary between the tip region 102 of the endodontic file 100 and the shank region 104 of the endodontic file 100, in other embodiments the rake angles of each endodontic file 100 in the series may be constant between the tip region 102 of the endodontic file 100 and the shank region 104 of the endodontic file 100. Furthermore, it should be recognized that, while the rake angle of each endodontic file 100 in a particular group is the same as, e.g., has the same values between the tip region 102 and the shank region 104, the rake angle of every other endodontic file 100 in the group, in other embodiments the rake angle of each endodontic file 100 of the series in a particular group is different from the rake angle of one or more other endodontic file 100 in the group. Still further, it should be recognized that, while the rake angle of each endodontic file 100 of the series may vary linearly between the tip region 102 of the endodontic file 100 and the shank region 104 of the endodontic file 100, in other embodiments the rake angles of each endodontic file 100 in the series may vary non-linearly between the tip region 102 and the shank region 104.

In one embodiment of the present invention, for each group of endodontic files 100, the cutting edge 110 of the endodontic file 100 defines a particular clearance angle that varies between the tip region 102 of the endodontic file 100 and the shank region 104 of the endodontic file 100. For instance, in one embodiment, each of a first group of endodontic files 100 has a clearance angle that is 0 degrees at the tip region 102 of the endodontic file 100 and that increases to a clearance angle of approximately 10 degrees at the shank region 104 of the endodontic file 100. In addition, each of a second group of endodontic files 100 also has a clearance angle that is 0 degrees at the tip region 102 of the endodontic file 100 and that increases to a clearance angle of approximately 10 degrees at the shank region 104 of the endodontic file 100. Also, each of a third group of endodontic file 100 has a clearance angle that is approximately 10 degrees at the tip region 102 of the endodontic file 100 and that increases to a clearance angle of approximately 20 degrees at the shank region 104 of the endodontic file 100. It should be recognized that, while the clearance angle of each endodontic file 100 of the series in one embodiment varies between the tip region 102 of the endodontic file 100 and the shank region 104 of the endodontic file 100, in other embodiments the clearance angles of each endodontic file 100 in the series may be constant between the tip region 102 of the endodontic file 100 and the shank region 104 of the endodontic file 100. Furthermore, it should be recognized that, while the clearance angle of each endodontic file 100 in a particular group is the same as, e.g., has the same values between the tip region 102 and the shank region 104, the clearance angle of every other endodontic file 100 in the group, in other embodiments the clearance angle of each endodontic file 100 in a particular group may be different from the clearance angle of one or more other endodontic file 100 in the group. Still further, it should be recognized that, while the clearance angle of each endodontic file 100 of the series in one embodiment may vary linearly between the tip region 102 of the endodontic file 100 and the shank region 104 of the endodontic file 100, in other embodiments the clearance angles of each endodontic file 100 in the series may vary non-linearly between the tip region 102 and the shank region 104.

In one embodiment of the present invention, for each group of endodontic files 100, the flutes 108 of the endodontic file 100 have a particular flute pitch that varies between the tip region 102 of the endodontic file 100 and the shank region 104 of the endodontic file 100. For instance, in one embodiment, each of a first group of endodontic files 100 has a flute pitch that is 10 degrees at the tip region 102 of the endodontic file 100 and that increases to a flute pitch of approximately 25 degrees at the shank region 104 of the endodontic file 100. In addition, each of a second group of endodontic files 100 also has a flute pitch that is 10 degrees at the tip region 102 of the endodontic file 100 and that increases to a flute pitch of approximately 25 degrees at the shank region 104 of the endodontic file 100. Also, each of a third group of endodontic files 100 has a flute pitch that is approximately 10 degrees at the tip region 102 of the endodontic file 100 and that increases to a flute pitch of approximately 25 degrees at the shank region 104 of the endodontic file 100. It should be recognized that, while the flute pitch of each endodontic file 100 of the series in one embodiment varies between the tip region 102 of the endodontic file 100 and the shank region 104 of the endodontic file 100, in other embodiments the flute pitch of each endodontic file 100 in the series may be constant between the tip region 102 of the endodontic file 100 and the shank region 104 of the endodontic file 100. Furthermore, it should be recognized that, while the flute pitch of each endodontic file 100 in a particular group is the same as, e.g., has the same values between the tip region 102 and the shank region 104, the flute pitch of every other endodontic file 100 in the group, in other embodiments the flute pitch of each endodontic file 100 in a particular group may be different from the flute pitch of one or more other endodontic file 100 in the group. Still further, it should be recognized that, while the flute pitch of each endodontic file 100 of the series in one embodiment may vary linearly between the tip region 102 of the endodontic file 100 and the shank region 104 of the endodontic file 100, in other embodiments the flute pitch of each endodontic file 100 in the series may vary non-linearly between the tip region 102 and the shank region 104.

In one embodiment of the present invention, for each group of endodontic files 100, the flutes 108 of the endodontic file 100 have a flute depth that varies between the tip region 102 of the endodontic file 100 and the shank region 104 of the endodontic file 100. For instance, in one embodiment, each of a first group of endodontic files 100 has a flute depth that is 15% at the tip region 102 of the endodontic file 100 and that increases to a flute depth of approximately 22% at the shank region 104 of the endodontic file 100. In addition, each of a second group of endodontic files 100 also has a flute depth that is 15% at the tip region 102 of the endodontic file 100 and that increases to a flute depth of approximately 22% at the shank region 104 of the endodontic file 100. Also, each of a third group of endodontic files 100 has a flute depth that is approximately 20% at the tip region 102 of the endodontic file 100 and that increases to a flute depth of approximately 22% at the shank region 104 of the endodontic file 100. It should be recognized that, while the flute depth of each endodontic file 100 of the series in one embodiment varies between the tip region 102 of the endodontic file 100 and the shank region 104 of the endodontic file 100, in other embodiments the flute depth of each endodontic file 100 in the series may be constant, or alternatively may decrease, between the tip region 102 of the endodontic file 100 and the shank region 104 of the endodontic file 100. Furthermore, it should be recognized that, while the flute depth of each endodontic file 100 in a particular group is the same as, e.g., has the same values between the tip region 102 and the shank region 104, the flute depth of every other endodontic file 100 in the group, in other embodiments the flute depth of each endodontic file 100 of the series in a particular group may be different from the flute depth of one or more other endodontic file 100 in the group. Still further, it should be recognized that, while the flute depth of each endodontic file 100 of the series in one embodiment may vary linearly between the tip region 102 of the endodontic file 100 and the shank region 104 of the endodontic file 100, in other embodiments the flute depth of each endodontic file 100 in the series may vary non-linearly between the tip region 102 and the shank region 104.

In one embodiment of the present invention, one or more of the endodontic files 100 may have a shank diameter, the diameter of the endodontic file near the proximal end, that is 1 mm or less. For instance, the endodontic files 100 may be manufactured from a nitinol blank that is, e.g., less than 0.9 mm, less than 0.8, less than 0.7 mm or less than 0.6 mm. By contrast, conventional endodontic files are typically manufactured from wires having a diameter that is greater than 1 mm, resulting in the removal of a large amount of metal from the wire during grinding and thereby changing the properties of the wire. The present invention, by employing a thinner wire, results in the removal of a smaller quantity of metal from the blank wire, thereby decreasing the likelihood that the properties of the wire will be adversely or undesirably effected. Still further, the use of a file shank having a smaller outer diameter than conventional endodontic files enables the file to better negotiate around the corners of the tooth during operation. It is also noted that the endodontic files of the present invention may have one or more abrasive surfaces thereon.

According to one embodiment of the present invention, the endodontic files 100 are manufactured by processing rods formed of nitinol. Advantageously, the rods from which the endodontic files 100 are formed are originally cylindrical in shape, and have a diameter of approximately 0.93 mm. The original cylindrically-shaped nitinol rods are then subjected to a first process. For the purposes of example only, the first process is referred to hereinafter as a grinding process, although other types of processes may be employed. In the first grinding process, the original cylindrically-shaped nitinol rods are ground so as to have a taper. Specifically, the original cylindrically-shaped nitinol rods are ground so as to form a tapered blank. Each tapered blank may have a diameter in the tip region and may have a taper such that the diameter of the tapered blank increases towards a shank region. As set forth more fully above, the tapered blank may have any one of the following approximate diameters in the tip region: 0.15 mm, 0.20 mm, 0.25 mm, 0.30 mm, 0.35 mm, 0.40 mm, 0.45 mm, 0.50 mm, 0.55 mm and 0.60 mm. Alternatively, the diameters in the tip regions of the tapered blanks may be slightly larger than the sizes listed hereinabove in order that, upon the performance of subsequent grinding processes, as described below, the diameters of the endodontic files 100 eventually are reduced to the sizes listed above. In addition, and as set forth more fully above, the tapered blank may have any one of the following tapers: 0.04 mm/mm, 0.06 mm/mm and 0.08 mm/mm.

The tapered blank is then subjected to a second process. For the purposes of example only, the first process is referred to hereinafter as a grinding process, although other types of processes may be employed. Specifically, in the second grinding process, a plurality of helical flutes are ground into the tapered blank so as to form, between adjacent pairs of helical flutes, a cutting edge. Preferably, the second grinding process includes passing the tapered blank over a grinding wheel at least twice and preferably four times, such that each helical flute, and consequently each cutting edge, is formed in at least two, and preferably between two and four, grinding steps.

According to one embodiment, a first side of each cutting edge, and consequently a first portion of a helical flute, is formed in a rake angle-forming step by passing the tapered blank twice over a grinding wheel. The tapered blank and the grinding wheel used in the two passes of the grinding wheel in this rake angle-forming step are configured so as to form, on the first side of the cutting edge, a rake angle. Preferably, the tapered blank and the grinding wheel used in the two passes of the grinding wheel in this rake angle-forming step are configured so as to form, on the first side of the cutting edge, a rake angle that varies between the tip region 102 and the shank region 104 of the endodontic file 100. For instance, and as set forth more fully above, the tapered blank and the grinding wheel used in the two passes of the grinding wheel in this rake angle-forming step may be configured so as to form, on the first side of the cutting edge, a rake angle that varies between approximately 5 degrees the tip region 102 and approximately 20 degrees the shank region 104 of the endodontic file 100, or a rake angle that varies between approximately 10 degrees the tip region 102 and approximately 20 degrees the shank region 104 of the endodontic file 100.

Furthermore, according to this embodiment, a second side of each cutting edge, and consequently a portion of a second helical flute, is formed in a clearance angle-forming step by passing the tapered blank over a grinding wheel. The tapered blank and the grinding wheel(s) used in the two passes of the grinding wheel in this clearance angle-forming step are configured so as to form, on the second side of the cutting edge, a clearance angle. Preferably, the tapered blank and the grinding wheel used in the two passes of the grinding wheel in this clearance angle-forming step are configured so as to form, on the second side of the cutting edge, a clearance angle that varies between the tip region 102 and the shank region 104 of the endodontic file 100.

The second grinding process also provides each flute 108 of each endodontic file 100 with a flute pitch. Specifically, the tapered blank and the grinding wheels used in the rake angle and/or the clearance angle-forming steps of the second grinding process are configured such that, during one or both of the rake angle and/or the clearance angle-forming steps of the second grinding process, flutes having a desired flute pitch are formed. Preferably, the tapered blank and the grinding wheel or wheels used in the two passes of the grinding wheel in the different grinding step are configured so as to form a flute having a flute pitch that varies between the tip region 102 and the shank region 104 of the endodontic file 100. For instance, and as set forth more fully above, the tapered blank and the grinding wheel or wheels used in the two passes of the grinding wheel in the clearance angle-forming step may be configured so as to form a flute having a flute pitch that varies between approximately 10 degrees at the tip region 102 and approximately 25 degrees at the shank region 104 of the endodontic file 100.

The second grinding process also provides each flute 108 of each endodontic file 100 with a flute depth. Specifically, the tapered blank and the grinding wheels used in the rake angle and/or the clearance angle-forming steps of the second grinding process are configured such that, during one or both of the rake angle and/or the clearance angle-forming steps of the second grinding process, flutes having a desired flute depth are formed. Preferably, the tapered blank and the grinding wheel or wheels used in the two passes of the grinding wheel in the different grinding step are configured so as to form a flute having a flute depth that varies between the tip region 102 and the shank region 104 of the endodontic file 100. For instance, and as set forth more fully above, the tapered blank and the grinding wheel or wheels used in the two passes of the grinding wheel in the clearance angle-forming step may be configured so as to form a flute having a flute depth that varies between approximately 15% at the tip region 102 and approximately 22% at the shank region 104 of the endodontic file 100, or having a flute depth that varies between approximately 20% at the tip region 102 and approximately 22% at the shank region 104 of the endodontic file 100.

In one embodiment of the present invention, the endodontic file is then subjected to a third process. Specifically, in the third process, the shank 105 of the endodontic file 100 is formed. As set forth more fully above, the shank 105 is formed in the third process so as to have a shape that, when viewed in cross-section, fits into a complementary shaped opening in a drill device or the like. In one embodiment, the shank 105 is formed from a material that is different from the material from which the endodontic file 100 is formed, and is attached to the endodontic file 100 after both the shank 105 and the endodontic file 100 have been separately formed. In this case, the shank may be welded, heat shrunk or otherwise attached to the endodontic file 100. Preferably, however, the shank 105 is integrally formed with the endodontic file 100 such that the third process is a grinding process in which, by passing the endodontic file 100 over a grinding wheel, a portion of the original material of the endodontic file 100 is ground into the desired shape for detachably mating with a drill device or the like.

In one embodiment of the present invention, the first and second processes are performed simultaneously. Thus, the endodontic file is manufactured by simultaneously forming a taper on the file body from the tip region towards the shank region and forming at least two helical flutes in the file body. In this manner, the manufacturing time for each file may be reduced because the file is not subjected to two different and sequentially-performed processing, e.g., grinding, steps, but rather a single processing, e.g., grinding, step. For example, endodontic files are conventionally manufactured by first grinding a taper on a blank wire, e.g., a wire that originally has an outer diameter that is constant over its length. Once tapered, flutes are then ground into the wires. In order to accurately grind the flutes into the tapered wires, the tapered wires are typically supported within a similarly tapered notch of a file support, thereby ensuring that the tapered wire is not radially deflected during the grinding of the flutes.

The present invention, according to one embodiment, may employ one or more grinding wheels that simultaneously form a taper on a blank wire, which is preferably formed from nitinol, and form at least two helical flutes in the blank wire. The grinding wheels may be adjustable via control mechanisms in accordance with and controlled by software that is specifically configured for such purposes. In addition, the control mechanisms may include a file support that has a notch for supporting the file during the grinding process. The file support having the notch for supporting the file may also be adjustable in accordance with and controlled by software that is specifically configured for such purposes, so as to maintain the file support and notch in an appropriate position to thereby prevent the file from radially moving or deflecting when being ground. As set forth more fully above, the taper-forming and flute-forming processes may each be a grinding process, although other processes may be employed.

In one embodiment of the present invention, the endodontic files may be manufactured using lubricating oil that is cooled and re-cycled. For instance, according to one method of manufacturing the endodontic file, a nitinol wire is ground so as to form the endodontic file. This grinding process may include grinding a taper on a blank wire, grinding flutes into the wires, or else simultaneously performing both of these steps.

During this grinding process, a quantity of oil may be applied to the wire, such as by inlet openings in the grinding chamber of a machine performing the grinding steps. The quantity of oil may provide lubrication so that the material properties of the wire are not undesirably changed during the grinding process and to prevent breakage of the wire. The quantity of oil is then collected, such as by a collection device located underneath the wire or at the bottom of the grinding chamber.

The quantity of oil may then be cooled, such as by being passed through a cooling unit configured for this purpose. The cooling unit may operate to lower the temperature of the oil. Next, the quantity of oil may be re-cycled, e.g., re-applied to the wire as the wire continues to undergo the grinding process or else applied to additional wires during a grinding process. In this manner, the wire is not adversely effected by the temperature of the oil that is being used during grinding or other processing steps. This may be of particular importance when the endodontic file is manufactured from nitinol wire, as the properties of the nitinol may be undesirably changed if, during a grinding process, the temperature of the nitinol is significantly raised. The cooling of the lubricating, e.g., cutting, oil may help the endodontic file maintain a desired degree of elasticity and shape memory.

Figure 5A:
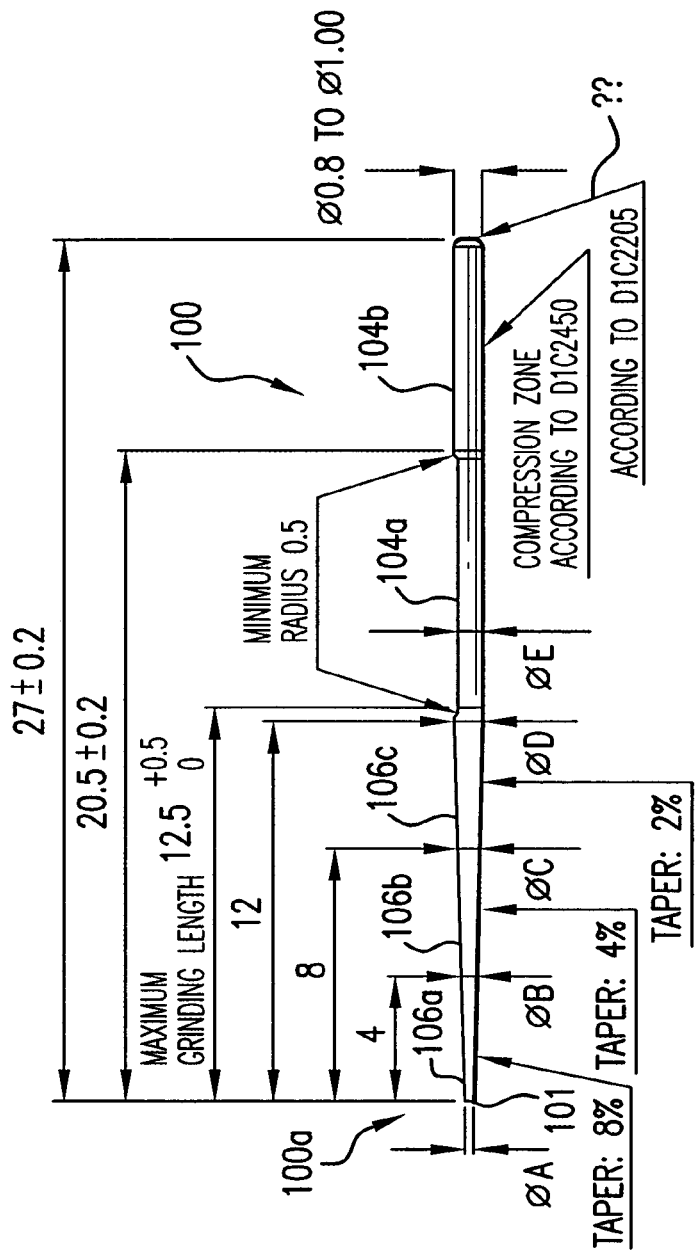
FIG. 5(a) is a side view of a first endodontic file body configuration, according to one example embodiment of the present invention.
Figure 6A:
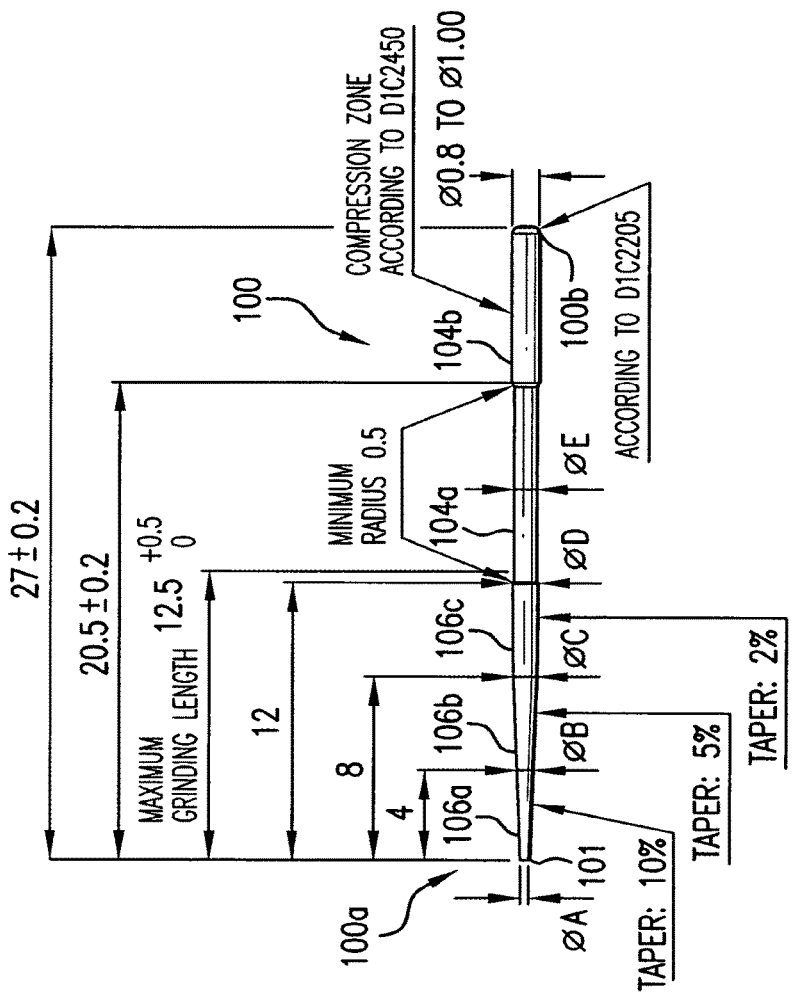
FIG. 6(a) is a side view of a first endodontic file body configuration, according to one example embodiment of the present invention.
Figure 7A:
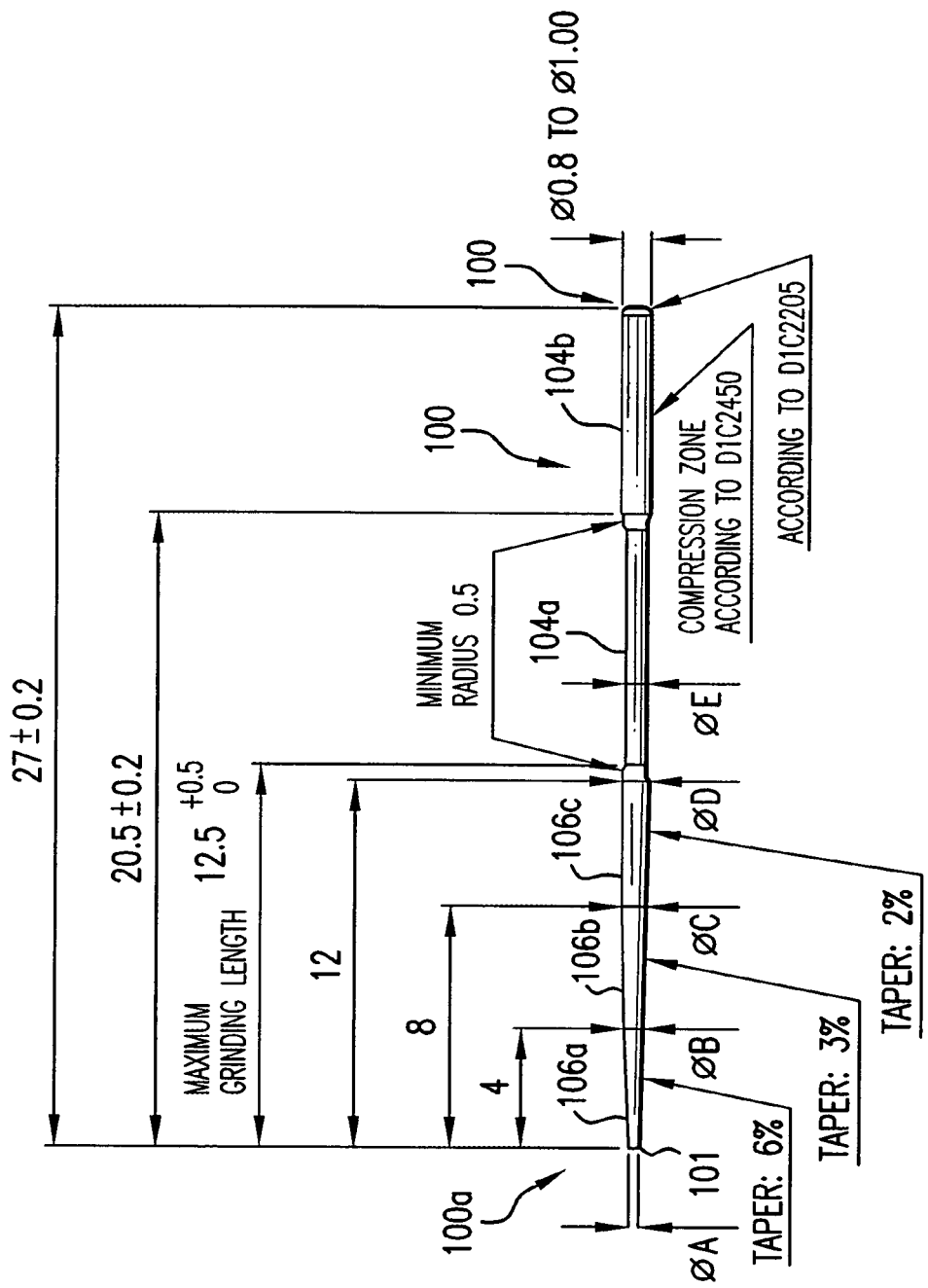
FIG. 7(a) is a side view of a first endodontic file body configuration, according to one example embodiment of the present invention.

According to one embodiment, each endodontic file is formed by a file body 100. The file body 100 is preferably formed from a single piece of metal, e.g., nitinol. FIGS. 5(a), 6(a) and 7(a) illustrate several configurations of a file body 100, each configuration having a specific tip size and taper arrangement for optimizing the removal of tissue from a root canal when used during a root canal procedure. These figures are further discussed below.

Mounted on the file bodies 100 are a stopper ring 200 and a shank mating arrangement 300. The stopper ring 200 and the shank mating arrangement 300 may be formed, e.g., integral, with the file body 100 using a single piece of metal, e.g., nitinol, or may be separately formed and subsequently mounted after the file body 100 has already been formed.

Referring now to FIGS. 5(a), 6(a) and 7(a), the following is a general list of some of the features of the endodontic file body 100, as illustrated therein:

100: total endodontic file body;
100a: distal-most end of file body;
100b: proximal-most end of file body;
101: tip;
104: shank region, e.g., extends from proximal-most end of file body 100b to the beginning of the working length 106;
106: working length, e.g., extends from tip 101 to the start of shank region 104; may be formed of working length portions 106a, 106b and 106c designated as, e.g., three portions of the working length; and
120: outside diameter of the file.

More specifically, each endodontic file body 100 includes a tip 101 at the distal-most end 100a of the endodontic file body 100. The tip 101 may be any type of drill tip but is preferably a non-cutting type of file tip. The use of a non-cutting type of file tip may help prevent the tip of the file from binding, particularly when the file tip is advanced sufficiently so as to emerge from the apex of the canal of the root. Each endodontic file body 100 includes a shank region 104 at the proximal end 100b of the endodontic file body 100. The shank region 104 may be formed of a first shank portion 104a and a second shank portion 104b, the first shank portion 104a being located distally relative to the second shank portion 104b. The second shank portion 104b is preferably employed for mounting the shank mating arrangement 300 onto the file body 100.

Each endodontic file body 100 also includes a working length 106 that extends from the tip 101 to the shank region 104. The working length 106 may include at least one helical flute 8. Preferably, the working length 106 of the endodontic file body 100 includes three helical flutes. Located between each pair of adjacent flutes and defined thereby is a respective cutting edge.

In accordance with the present invention, the first shank portion 104a has an outer diameter that is smaller than at least a portion of the outer diameter of some portion of the working length 106. Preferably, the first shank portion 104a has an outer diameter that is smaller than the largest outer diameter of the working length portion 106c immediately adjacent to the first shank portion 104a. The first shank portion 104a may or may not have flutes situated thereon. Advantageously, the outer diameter of the first shank portion 104a is sized relative to the working length 106, and particularly to the working length portion 106c, so as to insure that tissue that is removed by the cutting edges along the working length 106 may travel along the file body 100 without any portion of the file body 100 being clogged.

The endodontic file body 100 is tapered over at least a portion of the working length 106 so that an outer diameter of the endodontic file body 100 at the tip 101, e.g., the diameter of a circle that circumscribes the cutting edges at the tip region 101, is smaller than an outer diameter of the endodontic file body 100 adjacent to the shank region 104, e.g., the diameter of a circle that circumscribes the cutting edges along the working length portion 106c. A file body taper according to the various embodiments set forth herein may provide for decreased friction during operation, decreased torque and a reduced likelihood of breakage as more fully set forth above. Each of the file body 100 configurations illustrated in FIGS. 1(a), 2(a) and 3(a) employ a different taper scheme. Table 1 provides the dimensions, e.g., tip sizes, outer diameter dimensions, etc., of the first file body 100 configuration shown in FIG. 5(a). As provided therein, in this configuration, two different tip sizes, e.g., 0.20 mm and 0.25 mm, are employed. In addition, the file body 100 has three working length portions 106a, 106b and 106c, having rates of taper of 6% (0.06 mm/mm), 3% (0.03 mm/mm) and 2% (0.02 mm/mm), respectively. Table 1 provides the maximum outer diameter dimensions, e.g., B, C and D, at locations 4 mm, 8 mm and 12 mm from the tip 101. Table 1 also provides that the first shank portion 104a has a reduced outer diameter, designated as E, relative to the maximum outer diameter dimension D of the working length portion 106c, thereby providing improved tissue removal during use. The first shank portion 104a may have one or more small step or tapered regions located immediately adjacent to the working length portion 106c. For instance, between 12 mm and 12.5 mm from the tip 101, the first shank portion 104a steps or is tapered down in size. Likewise, at about 20.5 mm from the tip 101, the first shank portion 104a steps or is tapered up in size until it achieves an outer diameter dimension of 0.8 mm along the second shank portion 104b.

Table 2 provides the dimensions, e.g., tip sizes, outer diameter dimensions, etc., of the second file body 100 configuration shown in FIG. 6(a). As provided therein, in this configuration, three different tip sizes, e.g., 0.20 mm, 0.25 mm and 0.30 mm, are employed. In addition, the file body 100 has three working length portions 106a, 106b and 106c, having rates of taper of 8% (0.08 mm/mm), 4% (0.04 mm/mm) and 2% (0.02 mm/mm), respectively.

Table 2 provides the maximum outer diameter dimensions, e.g., B, C and D, at locations 4 mm, 8 mm and 12 mm from the tip 101. Table 2 also provides that the first shank portion 104a has a reduced outer diameter, designated as E, relative to the maximum outer diameter dimension D of the working length portion 106c, thereby providing improved tissue removal during use. The first shank portion 104a may have one or more small step or tapered regions located immediately adjacent to the working length portion 106c. For instance, between 12 mm and 12.5 mm from the tip 101, the first shank portion 104a steps or is tapered down in size. Likewise, at about 20.5 mm from the tip 101, the first shank portion 104a steps or is tapered up in size until it achieves an outer diameter dimension of 0.8 mm, or alternatively 1 mm, along the second shank portion 104b.

Table 3 provides the dimensions, e.g., tip sizes, outer diameter dimensions, etc., of the second file body 100 configuration shown in FIG. 7(a). As provided therein, in this configuration, one tip size, e.g., 0.30 mm, is employed. In addition, the file body 100 has three working length portions 106a, 106b and 106c, having rates of taper of 10% (0.10 mm/mm), 5% (0.05 mm/mm) and 2% (0.02 mm/mm), respectively. Table 3 provides the maximum outer diameter dimensions, e.g., B, C and D, at locations 4 mm, 8 mm and 12 mm from the tip 101. Table 3 also provides that the first shank portion 104a has a reduced outer diameter, designated as E, relative to the maximum outer diameter dimension D of the working length portion 106c, thereby providing improved tissue removal during use. The first shank portion 104a may have one or more small step or tapered regions located immediately adjacent to the working length portion 106c. For instance, between 12 mm and 12.5 mm from the tip 101, the first shank portion 104a steps or is tapered down in size. Likewise, at about 20.5 mm from the tip 101, the first shank portion 104a steps or is tapered up in size until it achieves an outer diameter dimension of 1 mm along the second shank portion 104b.

It should be recognized that these Figures and Tables provide merely one set of possible endodontic file bodies 100. Alternatively, the set may include any number of different files, taper configurations, number of working length portions, etc. Furthermore, the dimensions provided for the entire or any portion of the endodontic file, including the reduced shank diameter for each configuration, are simply illustrative and different dimensions may be employed within the scope of the present invention.

Figure 5B:
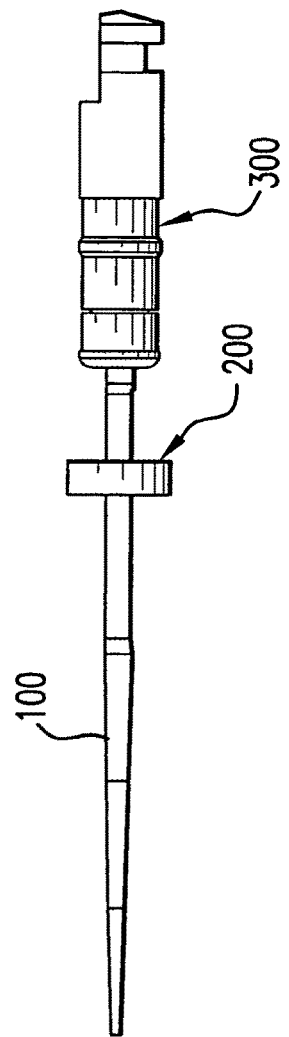
FIG. 5(b) is a side view of the first endodontic file body configuration of FIG. 5(a) including additional features.
Figure 6B:
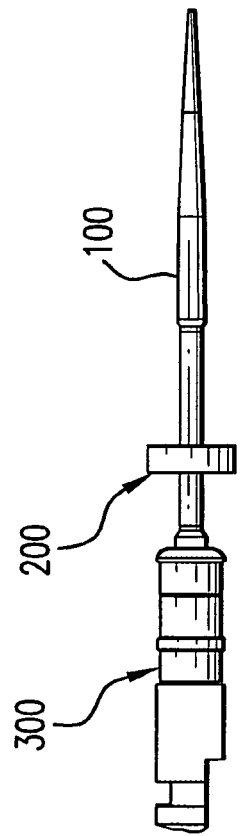
FIG. 6(b) is a side view of the first endodontic file body configuration of FIG. 6(a) including additional features.
Figure 7B:
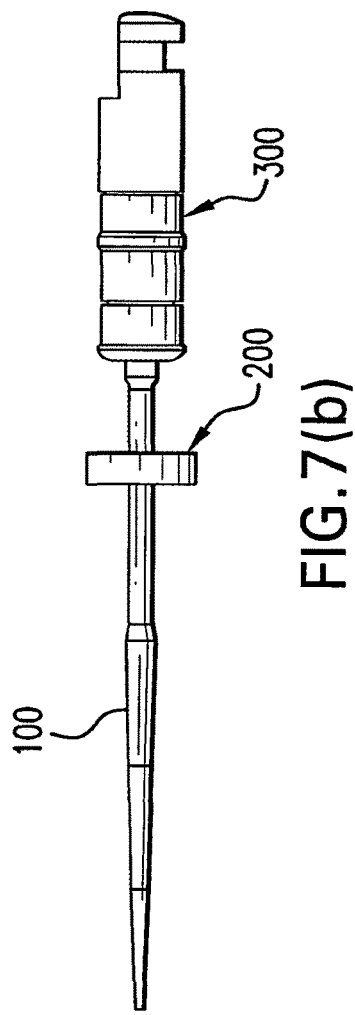
FIG. 7(b) is a side view of the first endodontic file body configuration of FIG. 7(a) including additional features.

Referring now to FIGS. 5(b), 6(b) and 7(b), the file bodies 100 are shown having the shank mating arrangement 300 mounted on the second shank portion 104b. The shank mating arrangement 300 may have any shape but preferably has a shape, when viewed in cross-section, that is configured to engage a complementary-shaped drill device for rotating the endodontic file body 100, as set forth more fully below. The shank mating arrangement 300 may also include an additional handle that allows the file body 100 to be gripped by a user's fingers or to be inserted into a drill or hand-piece. In addition, the shank mating arrangement 300 may include a size designation, e.g., a colored ring, a number or letter, etc., that enables a user to determine upon viewing it what is the size of the file body 100. Preferably, the shank mating arrangement 300 is attached to the file body 100 after the file body 100 is formed, for instance by heat-shrinking. In one embodiment, the shank 105 may be formed from a material, e.g., brass that is different from the material, e.g., nitinol, from which the endodontic file body 100 is formed, and is attached to the endodontic file body 100 after both the shank mating arrangement 300 and the endodontic file body 100 have been separately formed. Alternatively, the shank mating arrangement 300 is integrally formed with the endodontic file body 100.

It should be noted that the endodontic file bodies 100 of the present invention may be manufactured from a nitinol blank that is, e.g., 0.8 mm or 1 mm in diameter. By contrast, conventional endodontic files are typically manufactured from wires having a diameter that is greater than 1 mm, resulting in the removal of a large amount of metal from the wire during grinding and thereby changing the properties of the wire. The present invention, by employing a thinner wire, results in the removal of a smaller quantity of metal from the blank wire, thereby decreasing the likelihood that the properties of the wire will be adversely or undesirably effected.

The present invention, according to the other embodiments described hereinbelow, relates to an endodontic obturator device, a set of endodontic obturator devices, a method of manufacturing an endodontic obturator device and a method of manufacturing a set of endodontic obturator devices. It should be understood that the present invention is intended to cover each of these aspects. For instance, in accordance with various embodiments, the present invention relates to an endodontic obturator device, a set of endodontic obturator devices, a method of manufacturing an endodontic obturator device and a method of manufacturing a set of endodontic obturator devices wherein the endodontic obturator device(s) or of manufacturing the obturator device(s) may include one or more of the features described hereinbelow.

For example, the endodontic obturator device(s) of the present invention, such as those manufactured in accordance with the methods of the present invention, may comprise:

1) at least a portion extending from a tip region to a shank region;

2) a body defining a taper, wherein a rate of taper along at least a portion of the body relative to another portion from the tip region towards the shank region, may be one, one or more, or all:
  a) variable;
  b) non-constant;
  c) decreasing;
  d) increasing; and
  e) zero taper.

A series or set of endodontic obturator devices, as used hereinabove, may have the following characteristics with respect to tip and taper:

Tip

In one embodiment, the series or set of the obturator device has at least two with the same tip diameter. In one embodiment, the series or set of the obturator device has at least two with tip diameters that are within 0.025 mm of each other that will be considered to be the same tip diameter. In one embodiment, the series or set of the obturator device has at least two without the same tip diameter.

Taper

In one embodiment, the series or set of the obturator device has at least two with the same taper. In one embodiment, the series or set of the obturator device has at least two with tapers at similar portions that are within 0.01 mm/mm of each other that will be considered to be the same taper. In one embodiment, the series or set of the obturator device has at least two without the same taper.

The term "device" as used hereinabove may be defined as, for instance, a cone, appliance, or carrier. It may be made of gutta-percha, polymer, metal, or other material;

and may be used to fill a root canal space whether alone or covered with a material;

The obturator device may or may not have the following features or characteristics:
- it may be a single unit or multiple units
- it may have a handle, attached or unattached, as one unit or multiple separate units, made of similar or dissimilar materials or configurations;
- it may have:
  - length indicator markings;
  - grooves;
  - a smooth surface;
  - homogeneous or multiple layers of multiple or single materials being
- at least one form of gutta-percha, polymer, metal, or other material.

In various embodiments, the present invention includes features corresponding to the body of the endodontic obturator device. For instance, the present invention may include the following features along at least a portion of the endodontic obturator device.

In one embodiment, the rate of taper along at least a portion of the obturator device body decreases linearly between the tip region and the shank region.

In one embodiment, the rate of taper along at least a portion of the body decreases non-linearly between the tip region and the shank region.

In one embodiment, the rate of taper along the entire body decreases from the tip region towards the shank region.

In one embodiment, the rate of taper along the entire body decreases linearly between the tip region and the shank region.

In one embodiment, the rate of taper along the entire body decreases non-linearly between the tip region and the shank region.

In one embodiment, the at least two longitudinal portions are of equal length.

In one embodiment, the at least two longitudinal portions are of unequal length.

In one embodiment, the body includes three or more longitudinal portions.

In one embodiment, the three or more longitudinal portions are of equal length.

In one embodiment, the three or more longitudinal portions are of unequal length.

In one embodiment, the three or more longitudinal portions may have two or more portions of equal length.

In one embodiment, the three or more longitudinal portions may have two or more portions of unequal length.

In one embodiment, a rate of taper for one of the longitudinal portions of the body differs from a rate of taper for another of the longitudinal portions of the body by at least 0.01.

In one embodiment, a rate of taper for one of the longitudinal portions of the body differs from a rate of taper for another of the longitudinal portions of the body by at least 0.02.

In one embodiment, a rate of taper for one of the longitudinal portions of the body differs from a rate of taper for another of the longitudinal portions of the body by at least 0.03.

In one embodiment, a rate of taper for one of the longitudinal portions of the body differs from a rate of taper for another of the longitudinal portions of the body by at least 0.04.

In one embodiment, a rate of taper for one of the longitudinal portions of the body differs from a rate of taper for another of the longitudinal portions of the body by 0.01 or less.

In one embodiment, a rate of taper for one of the longitudinal portions of the body differs from a rate of taper for another of the longitudinal portions of the body by 0.02 or less.

In one embodiment, a rate of taper for one of the longitudinal portions of the body differs from a rate of taper for another of the longitudinal portions of the body by 0.03 or less.

In one embodiment, a rate of taper for one of the longitudinal portions of the body differs from a rate of taper for another of the longitudinal portions of the body by 0.04 or less.

In one embodiment, the body has at least three (3) different portions of rates of taper along the body where the 2nd portion is in a decreasing rate of taper compared to the adjacent 1st portion. The 2nd portion may be decreasing at a constant or non-constant rate of taper and at multiple different decreasing rates of taper. The 3rd portion is at an increasing rate of taper compared to the adjacent 2nd portion.

In one embodiment, the body has at least three (3) different portions of rates of taper along the body where the 2nd portion is in an increasing rate of taper compared to the adjacent 1st portion. The 2nd portion may be increasing at a constant or non-constant rate of taper and at multiple different increasing rates of taper. The 3rd portion is at a decreasing rate of taper compared to the adjacent 2nd portion.

Several embodiments of the present invention are specifically illustrated and/or described herein. However, it will be appreciated that modifications and variations of the present invention are covered by the above teachings without departing from the spirit and intended scope of the present invention.

What is claimed is:

1. An endodontic obturator, comprising:
   a tip region at a distal end of the obturator;
   a shank region at a proximal end of the obturator;
   at least one obturator portion between the tip region and the shank region, the at least one obturator portion configured to at least partially enter a root canal of a tooth over its length and comprising a body defining a taper; and
   a material layer containing gutta-percha, rubber, or resin applied to the body;
   wherein the at least one obturator portion includes, in a direction from the tip region towards the shank region, a first tapered obturator portion, a second tapered obturator portion, and a third tapered obturator portion,
   wherein each of the first tapered obturator portion, the second tapered obturator portion, and the third tapered obturator portion are tapered in a longitudinal direction of the body and have a solid cross section throughout a width of the obturator,
   wherein respective rates of taper along respective portions of the body differ between the first tapered obturator portion, the second tapered obturator portion, and the third tapered obturator portion,
   wherein the different rates of taper along each of the first tapered obturator portion, the second tapered obturator portion, and the third tapered obturator portion relative to each other are one of variable, decreasing, and increasing, wherein the first tapered obturator portion, the second tapered obturator portion, and the third tapered obturator portion are of equal length, and each tapered obturator portion includes only one rate of taper, and wherein the first tapered obturator portion is adjacent to the second tapered obturator portion and the rate of taper for the first tapered obturator portion is greater than the rate of taper for the second tapered obturator portion, and the second tapered obturator portion is adjacent to the third tapered obturator portion and the rate of taper for the second tapered obturator portion is greater than the rate of taper for the third tapered obturator portion.

2. The endodontic obturator recited in claim 1, wherein a tip size of the obturator is selected from the group consisting of 0.10, 0.15, 0.20, 0.25, 0.30, 0.35, 0.40, 0.45, 0.50, 0.55 and 0.60 mm.

3. The endodontic obturator recited in claim 2, wherein the rate of taper of the first tapered obturator portion closer to the tip region is selected from the group consisting of 0.02, 0.03, 0.04, 0.05, 0.06, 0.07, 0.08, 0.09, and 0.10 mm/mm or less.

4. The endodontic obturator recited in claim 2, wherein the rate of taper of the second tapered obturator portion closer to the shank region is selected from the group consisting of 0.02, 0.03, 0.04, 0.05, 0.06, 0.07, 0.08, 0.09, 0.10 mm/mm or less.

5. The endodontic obturator recited in claim 1, wherein the obturator is comprised of a polymer.

6. The endodontic obturator recited in claim 1, wherein the obturator has a handle that is larger than the shank region.

7. The endodontic obturator recited in claim 1, wherein the obturator has a matte finish.

8. The endodontic obturator recited in claim 1, wherein the obturator has a smooth finish.

9. The endodontic obturator recited in claim 1, wherein the at least one obturator portion has an ovoid cross-section.

* * * * *